(12) United States Patent
Luttun et al.

(10) Patent No.: US 10,967,006 B2
(45) Date of Patent: Apr. 6, 2021

(54) STEM CELLS FOR WOUND HEALING

(71) Applicants: ABT Holding Company, Cleveland, OH (US); Katholieke Universiteit Leuven, Leuven (BE)

(72) Inventors: Aernout Luttun, Zwevezele (BE); Robert J Deans, Riverside, CA (US)

(73) Assignees: ABT Holding Company, Cleveland, OH (US); Katholieke Universiteit Leuven, Leuven (BE)

(*) Notice: Subject to any disclaimer, the term of this patent is extended or adjusted under 35 U.S.C. 154(b) by 0 days.

(21) Appl. No.: 15/043,171

(22) Filed: Feb. 12, 2016

(65) Prior Publication Data

US 2017/0209493 A1 Jul. 27, 2017

Related U.S. Application Data

(60) Provisional application No. 62/281,334, filed on Jan. 21, 2016.

(51) Int. Cl.
| | | |
|---|---|---|
| *A61K 35/28* | (2015.01) | |
| *A61K 35/12* | (2015.01) | |
| *C12N 5/074* | (2010.01) | |
| *A61P 17/02* | (2006.01) | |

(52) U.S. Cl.
CPC .............. *A61K 35/28* (2013.01); *A61K 35/12* (2013.01); *A61P 17/02* (2018.01); *C12N 5/0607* (2013.01); *A01K 2207/12* (2013.01); *A01K 2227/105* (2013.01); *A01K 2267/03* (2013.01)

(58) Field of Classification Search
None
See application file for complete search history.

(56) References Cited

U.S. PATENT DOCUMENTS

| | | | |
|---|---|---|---|
| 5,486,359 | A | 1/1996 | Caplan et al. |
| 5,827,735 | A | 10/1998 | Young et al. |
| 5,906,934 | A | 5/1999 | Grande et al. |
| 6,077,987 | A | 6/2000 | Breitbart et al. |
| 6,090,625 | A | 7/2000 | Abuljadayel |
| 6,214,369 | B1 | 4/2001 | Grande et al. |
| 6,398,816 | B1 | 6/2002 | Breitbart et al. |
| 6,653,134 | B2 | 11/2003 | Prockop et al. |
| 6,777,231 | B1 | 8/2004 | Katz et al. |
| 7,015,037 | B1 | 3/2006 | Furcht et al. |
| 7,045,148 | B2 | 5/2006 | Radii |
| 7,056,738 | B2 | 6/2006 | Prockop et al. |
| 7,229,827 | B2 | 6/2007 | Kim et al. |
| 7,311,905 | B2 | 12/2007 | Hariri |
| 7,659,118 | B2 | 2/2010 | Furcht et al. |
| 7,794,706 | B2 | 9/2010 | Carpenter et al. |
| 7,838,289 | B2 | 11/2010 | Furcht et al. |
| 7,883,892 | B2 | 2/2011 | Verfaillie et al. |
| 7,927,587 | B2 | 4/2011 | Blazer et al. |
| 8,075,881 | B2 | 12/2011 | Verfaillie et al. |
| 8,147,824 | B2 | 4/2012 | Maziarz et al. |
| 8,192,348 | B2 | 6/2012 | Tranquillo et al. |
| 8,252,280 | B1 | 8/2012 | Verfaillie et al. |
| 8,409,859 | B2 | 4/2013 | Verfaillie et al. |
| 8,426,200 | B2 | 4/2013 | Verfaillie et al. |
| 8,551,470 | B2 | 10/2013 | Son et al. |
| 8,580,249 | B2 | 11/2013 | Blazar et al. |
| 8,603,462 | B2 | 12/2013 | Westenfelder |
| 8,609,406 | B2 | 12/2013 | Subramanian et al. |
| 8,609,412 | B2 | 12/2013 | Panoskaltsis-Mortari et al. |
| 8,822,215 | B2 | 9/2014 | Hantash |
| 8,871,198 | B2 | 10/2014 | Emig et al. |
| 9,005,964 | B2 | 4/2015 | Verfaillie et al. |
| 9,057,051 | B2 | 6/2015 | Pauwelyn et al. |
| 9,090,878 | B2 | 7/2015 | Sancho-Bru et al. |
| 9,254,305 | B2 | 2/2016 | Son et al. |
| 9,347,045 | B2 | 5/2016 | Hantash |
| 9,382,514 | B2 | 7/2016 | Hantash |
| 9,388,388 | B2 | 7/2016 | Verfaillie et al. |
| 9,447,380 | B2 | 9/2016 | Subramanian et al. |
| 9,526,747 | B2 | 12/2016 | Verfaillie et al. |
| 9,617,513 | B2 | 4/2017 | Young et al. |
| 9,644,182 | B2 | 5/2017 | Baksh et al. |
| 9,682,105 | B2 | 6/2017 | Le et al. |
| 9,694,035 | B2 | 7/2017 | Aggarwal et al. |
| 9,700,601 | B2 | 7/2017 | Blazer et al. |
| 9,764,044 | B2 | 9/2017 | Verfaillie et al. |
| 9,777,258 | B2 | 10/2017 | Sancho-Bru et al. |
| 9,789,136 | B2 | 10/2017 | Furcht et al. |

(Continued)

FOREIGN PATENT DOCUMENTS

| | | |
|---|---|---|
| WO | 2009154840 | 12/2009 |
| WO | 2015/017772 | 2/2015 |
| WO | WO2017/062035 | 10/2015 |

OTHER PUBLICATIONS

Herdich et al. Multipotent adult progenitor cells; their role in wound healing and the treatment of dermal wounds. Cytotherapy 2008 10(6) 543-550.*
Wu et al., "Mesenchymal Stem Cells Enhance Wound Healing Through Differentiation and Angiogenesis," Stem Cells, 2007, p. 2648-2659, vol. 25(10).
Maruyama et al., "Decreased Macrophage Number and Activation Lead to Reduced Lymphatic Vessel Formation and Contribute to Impaired Diabetic Wound Healing," American Journal Pathology, Apr. 2007, p. 1178-1191, vol. 170.
Kerjaschki et al., "Lymphatic endothelial progenitor cells contribute to de novo lymphangiogenesis in human renal transplants", Nat Med, 2006, pp. 230-234, vol. 12.
Aranguren et al., "Multipotent Adult Progenitor Cells Sustain Function of Ischemic Limbs in Mice," J. Clin. Invest., 2008, p. 505-514, vol. 118.

(Continued)

*Primary Examiner* — Blaine Lankford
(74) *Attorney, Agent, or Firm* — Tarolli, Sundheim, Covell & Tummino LLP

(57) ABSTRACT

The present invention provides a method for treating wounds by applying cells as described in this application. In one aspect the method provides treatment for cutaneous wounds. In general embodiments the cells are delivered to the wound without being attached to a functionalized substrate in the delivery vehicle.

17 Claims, 12 Drawing Sheets

Specification includes a Sequence Listing.

(56) References Cited

U.S. PATENT DOCUMENTS

| | | |
|---|---|---|
| 9,808,485 B2 | 11/2017 | Maziarz et al. |
| 9,861,660 B2 | 1/2018 | LaFrancesca et al. |
| 2001/0033834 A1 | 10/2001 | Wilkison et al. |
| 2001/0046489 A1 | 11/2001 | Habener et al. |
| 2002/0061587 A1 | 5/2002 | Anversa |
| 2002/0164794 A1 | 11/2002 | Wernet |
| 2003/0003090 A1 | 1/2003 | Prockop et al. |
| 2003/0032179 A1 | 2/2003 | Hariri |
| 2003/0059414 A1 | 3/2003 | Ho et al. |
| 2004/0033214 A1 | 2/2004 | Young et al. |
| 2004/0235165 A1 | 11/2004 | Prockop et al. |
| 2005/0169896 A1 | 8/2005 | Li et al. |
| 2005/0181502 A1 | 8/2005 | Furcht et al. |
| 2005/0255588 A1 | 11/2005 | Young et al. |
| 2005/0283844 A1 | 12/2005 | Furcht et al. |
| 2006/0127373 A1 | 6/2006 | Son et al. |
| 2006/0177925 A1 | 8/2006 | Rosenberg et al. |
| 2006/0228798 A1 | 10/2006 | Verfaillie et al. |
| 2007/0178071 A1 | 8/2007 | Westenfelder |
| 2008/0113434 A1 | 5/2008 | Davies et al. |
| 2008/0194021 A1 | 8/2008 | Mays |
| 2008/0194024 A1 | 8/2008 | Mays |
| 2008/0311084 A1 | 12/2008 | Verfaillie et al. |
| 2008/0317740 A1 | 12/2008 | Blazar et al. |
| 2009/0104159 A1 | 4/2009 | Prosper et al. |
| 2009/0104163 A1 | 4/2009 | Deans et al. |
| 2009/0203129 A1 | 8/2009 | Furcht et al. |
| 2009/0203130 A1 | 8/2009 | Furcht et al. |
| 2009/0208463 A1 | 8/2009 | Pittenger et al. |
| 2009/0233353 A1 | 9/2009 | Furcht et al. |
| 2009/0233354 A1 | 9/2009 | Furcht et al. |
| 2010/0008890 A1 | 1/2010 | Mays et al. |
| 2010/0172885 A1 | 7/2010 | Pittenger et al. |
| 2010/0183519 A1 | 7/2010 | Katz et al. |
| 2010/0239542 A1 | 9/2010 | Young et al. |
| 2010/0239543 A1 | 9/2010 | Young et al. |
| 2010/0310570 A1 | 12/2010 | Mays et al. |
| 2011/0020292 A1 | 1/2011 | Van't Hof |
| 2011/0020293 A1 | 1/2011 | Woda et al. |
| 2011/0064701 A1 | 3/2011 | Young et al. |
| 2011/0070206 A1 | 3/2011 | Rubin et al. |
| 2011/0081326 A1 | 4/2011 | Hantash |
| 2011/0111492 A1 | 5/2011 | Hu et al. |
| 2011/0171659 A1 | 7/2011 | Furcht et al. |
| 2011/0177595 A1 | 7/2011 | Furcht et al. |
| 2011/0206647 A1 | 8/2011 | Woda et al. |
| 2011/0212069 A1 | 9/2011 | Hamilton et al. |
| 2011/0293578 A1 | 12/2011 | Busch et al. |
| 2011/0293642 A1 | 12/2011 | Mays |
| 2011/0305638 A1 | 12/2011 | Ting et al. |
| 2011/0311496 A1 | 12/2011 | Pittenger et al. |
| 2011/0318313 A1 | 12/2011 | Cox, Jr. et al. |
| 2011/0318314 A1 | 12/2011 | Aggarwal et al. |
| 2012/0009674 A1 | 1/2012 | Mays |
| 2012/0039855 A1 | 2/2012 | Atlas et al. |
| 2012/0219572 A1 | 8/2012 | Prockop et al. |
| 2012/0308531 A1 | 12/2012 | Pinxteren et al. |
| 2013/0004464 A1 | 1/2013 | Nadal-Ginard |
| 2013/0121973 A1 | 5/2013 | Hantash |
| 2013/0122521 A1 | 5/2013 | Hantash |
| 2013/0129686 A1 | 5/2013 | Highfill et al. |
| 2013/0243882 A1 | 9/2013 | Fu et al. |
| 2013/0295058 A1 | 11/2013 | Le et al. |
| 2013/0315882 A1 | 11/2013 | Hu et al. |
| 2014/0037596 A1 | 2/2014 | Woda et al. |
| 2014/0065109 A1 | 3/2014 | Son et al. |
| 2014/0086886 A1 | 3/2014 | Westenfelder |
| 2014/0134137 A1 | 5/2014 | Van't Hof |
| 2014/0161776 A1 | 6/2014 | Aggarwal et al. |
| 2014/0186307 A1 | 7/2014 | Busch et al. |
| 2014/0186954 A1 | 7/2014 | Pauwelyn et al. |
| 2014/0234267 A1 | 8/2014 | Panoskaltsis-Mortari et al. |
| 2014/0242629 A1 | 8/2014 | Woda et al. |
| 2014/0295442 A1 | 10/2014 | Hamilton et al. |
| 2014/0322135 A1 | 10/2014 | Roobrouck et al. |
| 2015/0010610 A1 | 1/2015 | Tom et al. |
| 2015/0093364 A1 | 4/2015 | Busch et al. |
| 2015/0118193 A1 | 4/2015 | Maziarz et al. |
| 2015/0267167 A1 | 9/2015 | Furcht et al. |
| 2015/0272997 A1 | 10/2015 | Aggarwal et al. |
| 2016/0069903 A1 | 3/2016 | Lakadamyali et al. |
| 2016/0129043 A1 | 5/2016 | Shi et al. |
| 2016/0175485 A1 | 6/2016 | Isseroff et al. |
| 2016/0256502 A1 | 9/2016 | Cox et al. |
| 2016/0282336 A1 | 9/2016 | Hamilton et al. |
| 2016/0326494 A1 | 11/2016 | Cunha et al. |
| 2017/0022472 A1 | 1/2017 | Pinxteren et al. |

OTHER PUBLICATIONS

Hocking et al., "Mesenchymal stem cells: Paracrine signaling and differentiation during cutaneous wound repair," Exp Cell Res., Aug. 15, 2010; pp. 2213-2219, vol. 316(14).

Hendrickx et al. "Integration of Blood Outgrowth Endothelial Cells in Dermal Fibroblast Sheets Promotes Full Thickness Wound Healing", Stem Cells, 2010, p. 1165-1177, vol. 28.

Maxon et al., "Concise Review: Role of Mesenchymal Stem Cells in Wound Repair," Stem Cells Translational Medicine, 2012, p. 142-149, vol. 1.

Klotz et al. "Cardiac lymphatics are heterogeneous in origin and respond to injury," Nature, Jun. 4,2015, pp. 62-67, vol. 522.

Martinez-Corral et al., "Non-Venous Origin of Dermal Lymphatic Vasculature," Circ. Res., 2015, pp. 1649-1654, 116.

Ny et al., "A genetic Xenopus laevis tadpole model to study lymphangiogenesis," Nat Med, 2005,11:998-1004.

Stanczuk et al. cKit Lineage Hemogenic Endothelium-Derived Cells Contribute to Mesenteric Lymphatic Vessels, Cell Reports, Mar. 17, 2015, doi: 10.1016/j.celrep.2015.02.026, p. 1708-1721, vol. 10.

Wilting et al., "Dual origin of avian lymphatics," 2006, Dev Bio / 292: 165-173.

Conrad et al., "Multipotent mesenchymal stem cells acquire a lymphendothelial phenotype and enhance lymphatic regeneration in vivo", 2009, Circuration119:281-289.

Salven et al., "VEGFR-3 and CD133 identify a population of CD34+ lymphatic/vascular endothelial precursor cells" 2003, Blood101:168-172.

Lee et al., "Podoplanin-Expressing Cells Derived From Bone Marrow Play a Crucial Role in Postnatal Lymphatic Neovascularization," Circulation, 2012, 1413-1425, 122.

Religa et al., "Presence of bone marrow-derived circulating progenitor endothelial cells in the newly formed lymphatic iessels," Blood, Dec. 15, 2005, p. 4184-4190, vol. 106 (13).

Jiang et al., "Hematopoietic Stem Cells Contribute to Lymphatic Endothelium", PLoS ONE, Nov. 2008, 3812, v. 3(11).

Hwang et al., "Therapeutic lymphangiogenesis using stem cell and VEGF-C hydrogel," Biomaterials, Jul. 2011, p. 1415-4423, vol. 32, iss. 19.

Yan et al., "Adipose-derived stem cells promote lymphangiogenesis in response to VEGF-C stimulation or TGF-beta1 Inhibition," Future Oncol., Dec. 2011, p. 1457-1473, vol. 7(12).

Toyserkani et al., "Stem cells show promising results for lymphoedema treatment—A literature review," 2015, J Plast Surg Hand Surg, p. 65-71, vol. 49.

Shimizu et al., "Therapeutic lymphangiogenesis with implantation of adipose-derived regenerative cells," J Am Heart Assoc, 2012, 1 :e000877.

Lee et al., "Generation of pure lymphatic endothelial cells from human pluripotent stem cells and their therapeutic affects on wound repair," Sci. Rep., Jun. 2015, 11019.

Aranguren et al., "In vitro and in vivo arterial differentiation of human multipotent adult progenitor cells," Blood, Mar. 15, 2007, p. 2634-2642, vol. 109.

Aranguren et al., "MAPC Transplantation Confers a More Durable Benefit Than AC133+ Cell Transplantation in Severe Hind Limb Ischemia," Cell Trans., 2011, p. 259-269, vol. 20.

Saito et al., "Lymphedema and Therapeutic Lymphangiogenesis," BioMed Res. Int'l., 2013, 6 pgs., vol. 2013, Art. ID 804675.

(56) References Cited

OTHER PUBLICATIONS

Pelacho et al., "Multipotent adult progenitor cell transplantation increases vascularity and improves left ventricular function after myocardial infarction," J Tissue Eng Regen Med, 2007, p. 51-59, vol. 1.
Van't Hof, et al., "Direct delivery of syngeneic and allogeneic large-scale expanded multipotent adult progenitor cells mproves cardiac function after myocardial infarct.," Cytotherapy, 2007, p. 477-467, vol. 9(5).
International Search Report for Application No. PCT/US2016/017848.
U.S. Appl. No. 15/784,019, filed Oct. 13, 2017, Multipotent Adults Stem Cells and Methods for Isolation.
U.S. Appl. No. 15/709,144, filed Sep. 19, 2017, Homologous Recombination in Multipotent Adult Progenitor Cells.
U.S. Appl. No. 10/945,528, filed Sep. 20, 2004, MAPC Generation of Muscle Tissue.
U.S. Appl. No. 14/627,767, filed Feb. 20, 2015, Vascular/Lymphatic Endothelial Cells.
U.S. Appl. No. 12/435,084, filed May 4, 2009, Kidney Derived Stem Cells and Method for Their Isolation, Differentiation and Use.
U.S. Appl. No. 11/808,933, filed Jun. 13, 2007, High Oct3/4 MAPCs and Methods Therefor.
U.S. Appl. No. 14/703,488, filed May 4, 2015, Reducing Inflammation Using Cell Therapy.
U.S. Appl. No. 15/864,862, filed Jan. 8, 2018, Improving Organs for Transplantation.
U.S. Appl. No. 09/404,895, filed Sep. 24, 1999, Pluripotent Embryonic-Like Stem Cells, Compositions, Methods and Uses Thereof.
U.S. Appl. No. 09/668,508, filed Sep. 22, 2000, Pluripotent Embryonic-Like Stem Cells, Compositions, Methods and Uses Thereof.
U.S. Appl. No. 09/820,320, filed Mar. 28, 2001, Pluripotent Embryonic-Like Stem Cells, Compositions, Methods and Uses Thereof.
U.S. Appl. No. 15/470,760, filed Mar. 27, 2017, Serum-Free Suspension Culturing of Non-Hematopoietic Progenitor Cells.
Prockop, Darwin J., Marrow Stromal Cells as Stem Cells for Nonhematopoietic Tissues, Science, 1997, pp. 71-74, vol. 276.
Bjornson, et al., Turning Brain Into Blood: A Hematopoietic Fate Adopted by Adult Neural Stem Cells In Vivo, Science, 1999, pp. 534-537, vol. 283(5401).
Pittenger, et al., Multilineage Potential of Adult Human Mesenchymal Stem Cells, Science, 1999, pp. 143-147, vol. 284.
Izadpanah, et al., Biologic Properties of Mesenchymal Stem Cells Derived From Bone Marrow and Adipose Tissue, J. Cell. Biochem., 2006, pp. 1285-1297, vol. 99.
Long, et al., Neural Cell Differentiation In Vitro From Adult Human Bone Marrow Mesenchymal Stem Cells, Stem Cells and Devel., 2005, pp. 65-69, vol. 14.
Moriscot, et al., Human Bone Marrow Mesenchymal Stem Cells Can Express Insulin and Key Transcription Factors of the Endocrine Pancreas Developmental Pathway upon Genetic and/or Microenvironmental Manipulation In Vitro, 2005, Stem Cells, pp. 594-604, vol. 23.
Sanchez-Ramos, et al., Adult Bone Marrow Stromal Cells Differentiate Into Neural Cells In Vitro, 2000, Exp. Neurol., pp. 247-256, vol. 164.
Eglitis, et al., Hematopoietic Cells Differentiate Into Both Microglia and Macroglia in the Brains of Adult Mice, 1997, Proc. Natl. Acad. Sci. USA, pp. 4080-4085, vol. 94.
Kopen, et al., Marrow Stromal Cells Migrate Throughout Forebrain and Cerebellum, and They Differentiate Into Astrocytes After Injection Into Neonatal Mouse Brains, 1999, Proc. Natl. Acad. Sci. USA, pp. 10711-10716, vol. 96.
Lagasse, et al., Purred Hematopoietic Stem Cells Can Differentitate Into Hepatocytes In Vivo, 2000, Nature Med., pp. 1229-1234, vol. 6(11).
Wang, et al., Cell Fusion is the Principal Source of Bone-Marrow-Derived Hepatocytes, 2003, Nature, pp. 897-901, vol. 422.
Giles, Jim, The Trouble With Replication, 2006, Nature, pp. 344-347, vol. 422.
Aldhous, et al., Fresh Questions on Stem Cell Findings, Mar. 24, 2007, NewScientist, pp. 12-13, vol. 13.
Brazelton, et al., From Marrow to Brain Expression of Neuronal Phenotypes in Adult Mice, 2000, Science, pp. 1775-1779, vol. 290.
Clarke, et al., Generalized Potential of Adult Neural Stem Cells, 2000, Science, pp. 1660-1663, vol. 288.
Johansson, et al., Neural Stem Cells in the Adult Human Brain, 1999, Exp. Cell Res., pp. 733-736, vol. 253.
Mezey, et al., Turning Blood Into Brain: Cells Bearing Neuronal Antigens Generated In Vivo From Bone Marrow, 2000, Science, pp. 1779-1782, vol. 290.
Morshead, et al., Hematopoietic Competence is a Rare Property of Neural Stem Cells That May Depend on Genetic and Epigenetic Alterations, 2002, Nature Med., pp. 268-273, vol. 8.
Petersen, et al., Bone Marrow as a Potential Source of Hepatic Oval Cells, 1999, Science, pp. 1168-1170, vol. 284.
Scintu, et al., Differentiation of Human Bone Marrow Stem Cells Into Cells With a Neural Phenotype: Diverse Effects of Two Specific Treatments, BMC Neurosci., 2006, vol. 7:14.
Wu, et al., Generation of Pancreatic β Cells From Mesenchymal Stem Cells to Treat Type 1 Diabetes, OA Stem Cells, Mar. 22, 2014, 2(1):5.
Guo, et al., Differentiation of Mesenchymal Stem Cells Into Dopaminergic Neuron-like Cells in Vitro, Biomed. and Enviro. Sol., 2005, pp. 36-42, vol. 18.
Piccinato, et al., High OCT4 and Low p16INK4A Expressions Determine in Vitro Lifespan of Mesenchymal Stem Cells, Stem Cells Int'l., 11 pages, vol. 2015, Article ID 369828.
Greco, et al., Functional Similarities Among Genes Regulated by Oct4 in Human Mesenchymal and Embryonic Stem Cells, Stem Cells, 2007, pp. 3143-3154, vol. 25.
Ong, et al., Hepatic Differentiation Potential of Commercially Available Human Mesenchymal Stem Cells, Tiss. Eng., 2006, pp. 3477-3485, vol. 12(12).
Ratajczak, et al. Very Small Embryonic Like (VSEL) Stem Cells—Characterization, Developmental Origin and Biological Significance, Exp Hematol., 2008, pp. 742-751, vol. 36(6).
Xiao, et al., Transplantation of a Novel Cell Line Population of Umbilical Cord Blood Stem Cells Ameliorates Neurological Deficits Associated With Ischemic Brain Injury, Stem Cells and Dev., 2005, pp. 722-733, vol. 14.
Yanjie, et al., Effects of Notch-I Signalling Pathway on Differentiation of Marrow Mesenchymal Stem Cells Into Neurons in Vitro, NeuroRep., Sep. 17, 2007, pp. 1443-1447, vol. 18(14).
Karaöz, et al., A Comprehensive Characterization Study of Human Bone Marrow MSCs with an Emphasis on Molecular and Ultrastructural Properties, J. Cell. Physiol., 2011, pp. 1367-1382, vol. 226.
Roche, et al., Oct-4, Rex-1, and Gata-4 Expression in Human MSC Increase the Differentiation Efficiency But Not hTERT Expression, J. Cell. Biochem., 2007, pp. 271-280, vol. 101.
Shuberg, Laura J., USPTO Non-final Office Action and Form 892 in U.S. Appl. No. 14/266,480, dated Apr. 20, 2018.
Shuberg, Laura J., USPTO Non-final Office Action and Form 892 in U.S. Appl. No. 13/071,801, dated May 3, 2018.
MacFarlane, Stacey Nee, USPTO Non-final Office Action and Form 892 in U.S. Appl. No. 13/062,343, dated Apr. 11, 2018.
Schuberg, Laura J., USPTO Final Office Action and Form 892 in U.S. Appl. No. 13/071,801, dated Mar. 5, 2019.
European Patent Office, Extended Supplementary Search Report and Written Opinion, dated Jul. 3, 2019, in corresponding European Application No. 16886758.8.
Kirby, et al., Stem Cells for Cutaneous Wound Healing, BioMed Res. Int'l., Jan. 1, 2015, pp. 1-11, vol. 2015.
Ji, et al., Rat Marrow-Derived Multipotent Adult Progenitor Cells Differentiate Into Skin Epidermal Cells In Vivo, J. Dermatol., Jul. 1, 2009, pp. 403-409, vol. 36(7).
Jahagirdar, et al., Multipotent Adult Progenitor Cell and Stem Cell Plasticity, Stem Cell Revs., Jan. 1, 2005, pp. 53-59, vol. 1(1).
Riekstina et al., Embryonic Stem Cell Marker Expression Pattern in Human Mesenchymal Stem Cells Derived from Sone Marrow, Adipose Tissue, Heart and Dermis, Stem Cell Rev. and Rep., 2009, 5:378-386.

(56) References Cited

OTHER PUBLICATIONS

Rosland et al., Long-Term Cultures of Bone Marrow-Derived Human Mesenchymal Stem Cells Frequently Undergo Spontaneous Malignant Transformation, Cancer Res., 2009, vol. 69(13), pp. 5331-5339.

Form 892, Notice of References Cited, Issued in U.S. Appl. No. 14/252,364, dated May 5, 2016 (citing Riekstina 2009).

Form 892, Notice of References Cited, Issued in U.S. Appl. No. 14/252,364, dated Feb. 2, 2017 (citing Rosland 2009).

Cha et al., Stem Cells in Cutaneous Wound Healing, Clinics in Dermatology, 2007, pp. 73-78, vol. 25.

\* cited by examiner

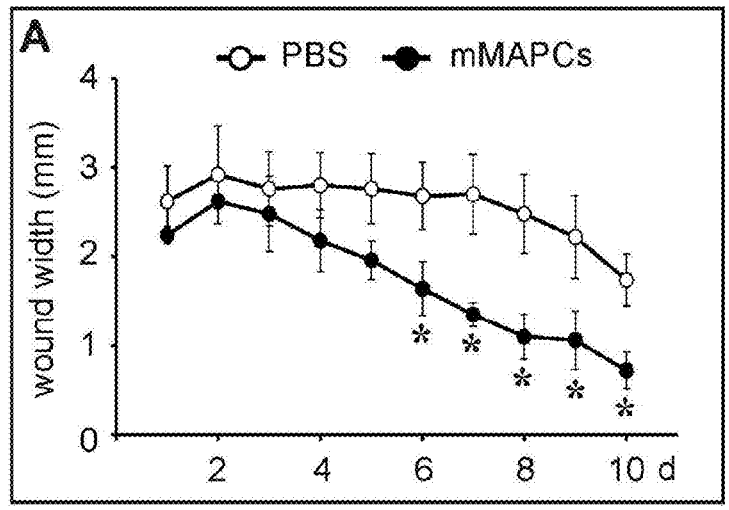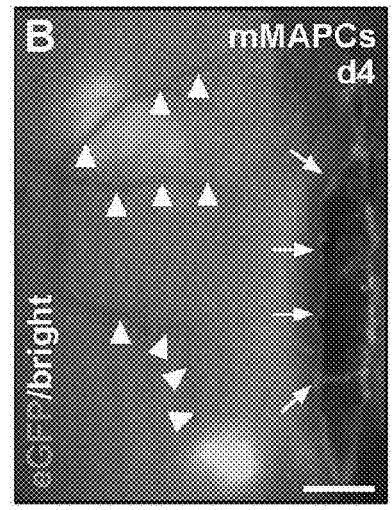
Fig. 2A                    Fig. 2B
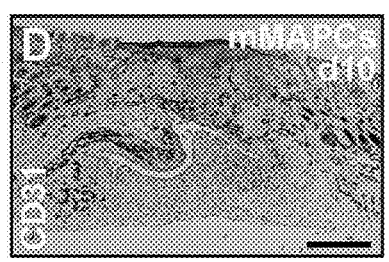
Fig. 2C                    Fig. 2D
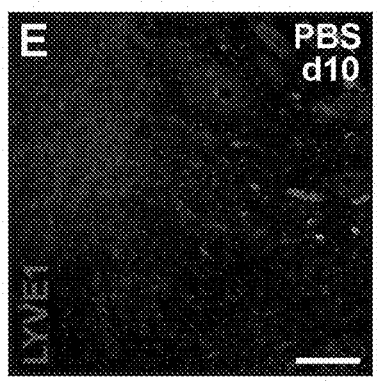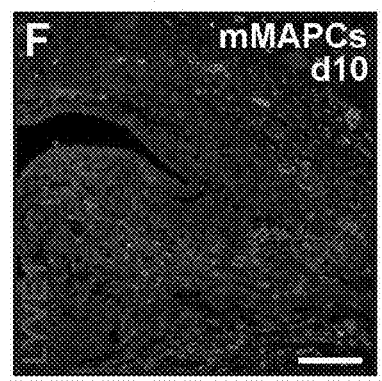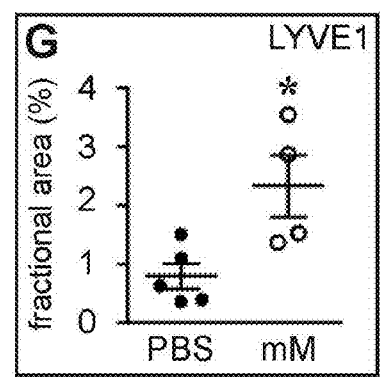
Fig. 2E           Fig. 2F           Fig. 2G

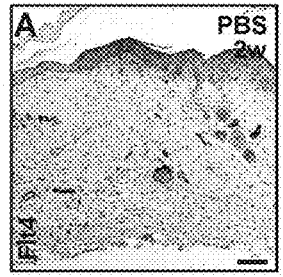 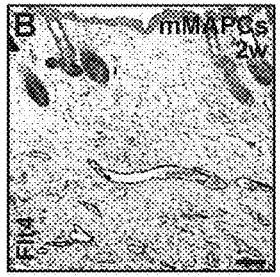 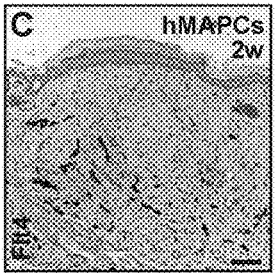 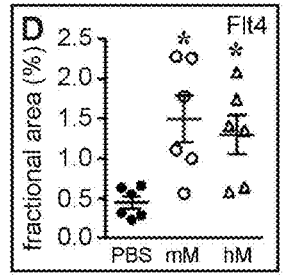
Fig. 4A    Fig. 4B    Fig. 4C    Fig. 4D
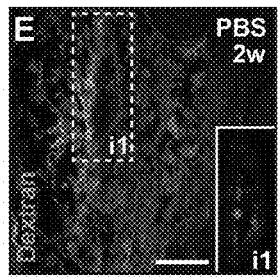 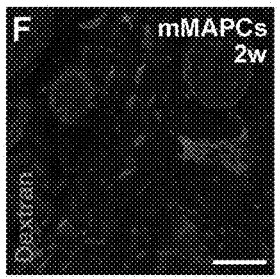 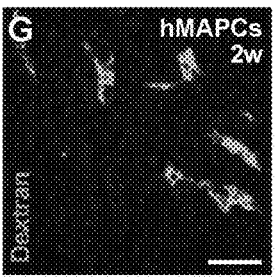 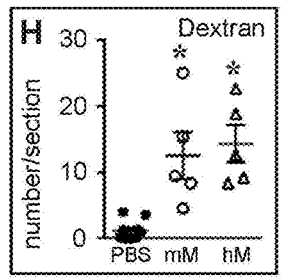
Fig. 4E    Fig. 4F    Fig. 4G    Fig. 4H
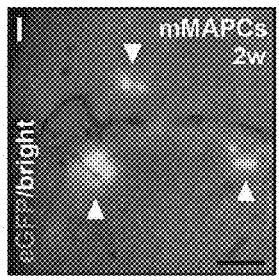 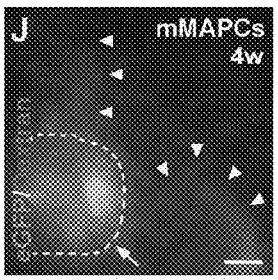 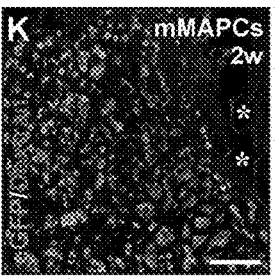 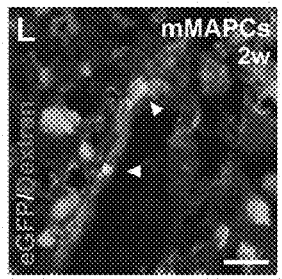
Fig. 4I    Fig. 4J    Fig. 4K    Fig. 4L

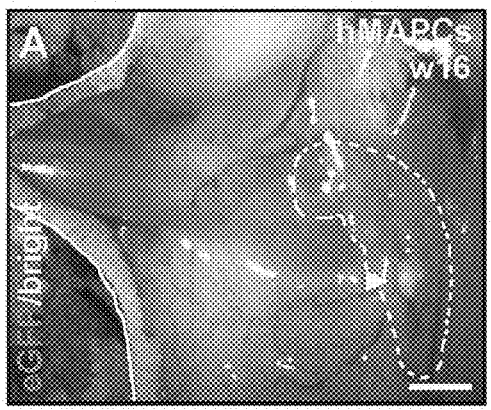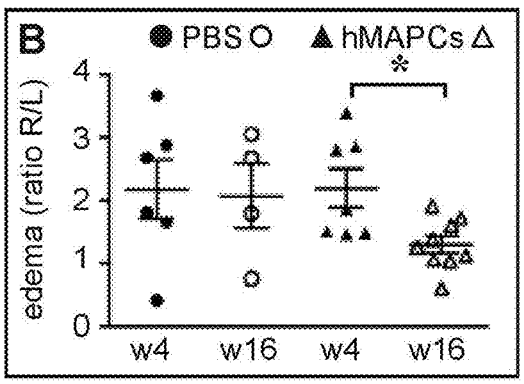
Fig. 5A  Fig. 5B
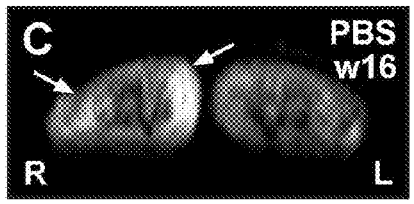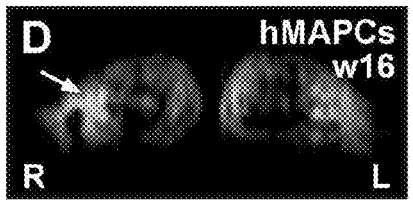
Fig. 5C  Fig. 5D
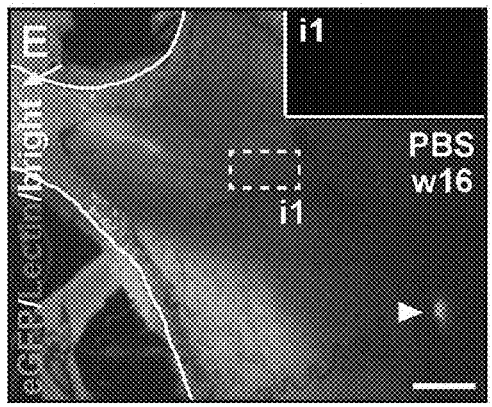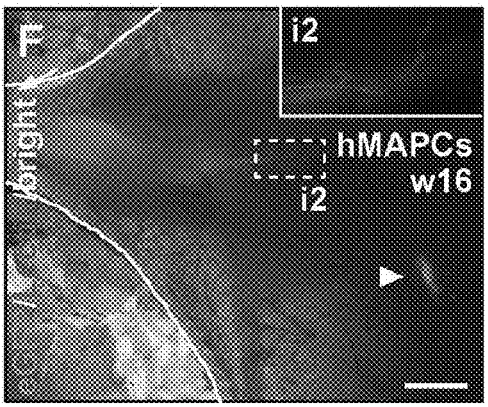
Fig. 5E  Fig. 5F
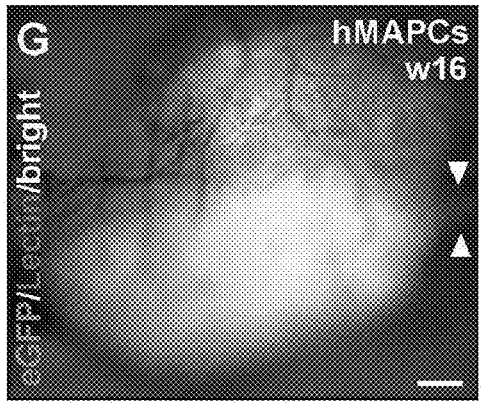
Fig. 5G

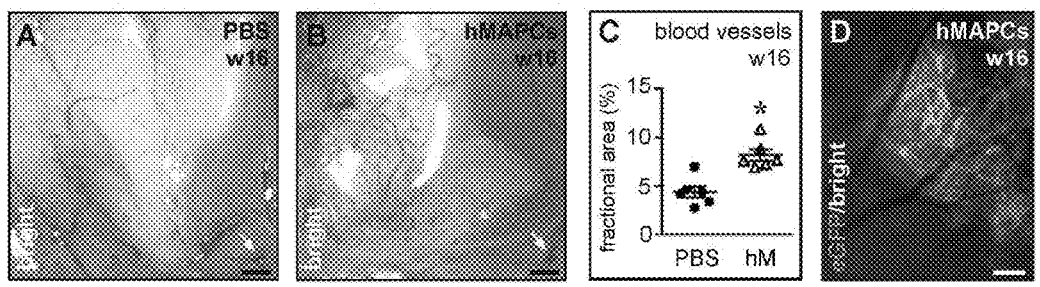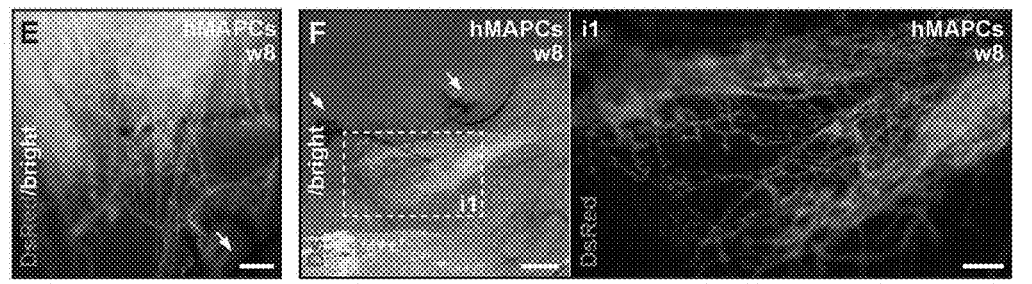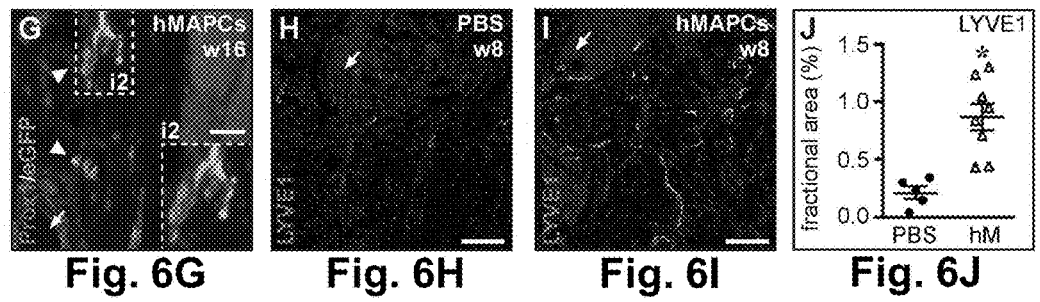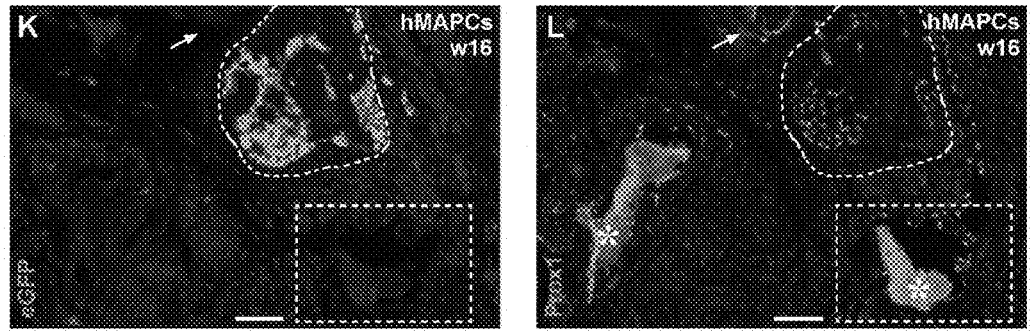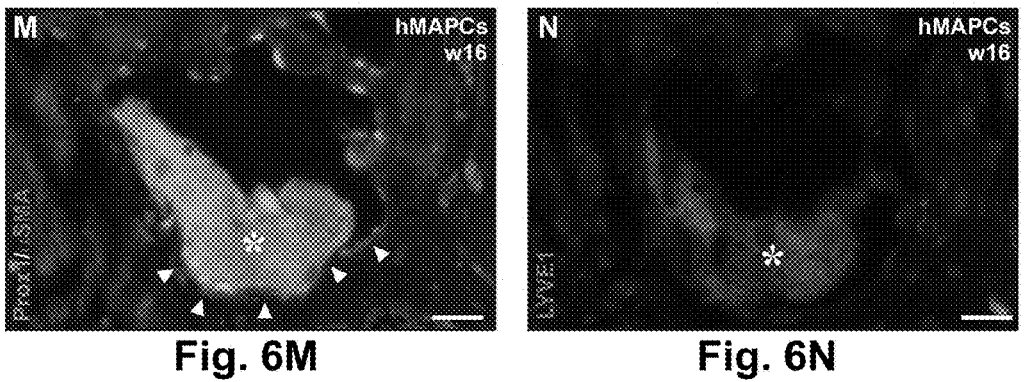
Fig. 6A Fig. 6B Fig. 6C Fig. 6D
Fig. 6E Fig. 6F
Fig. 6G Fig. 6H Fig. 6I Fig. 6J
Fig. 6K Fig. 6L
Fig. 6M Fig. 6N

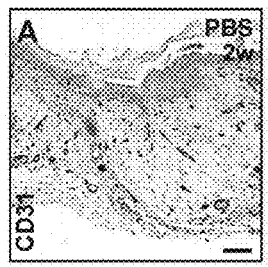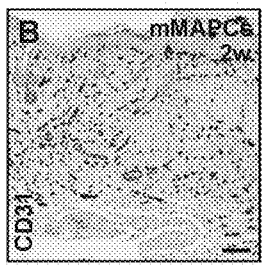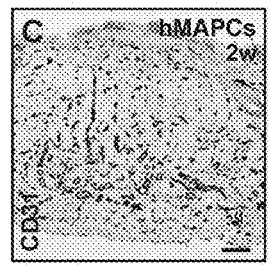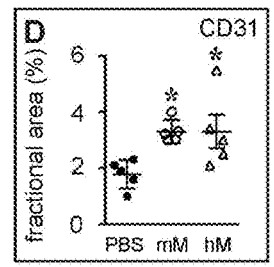
Fig. 8A  Fig. 8B  Fig. 8C  Fig. 8D
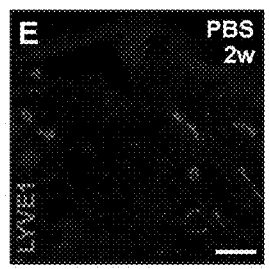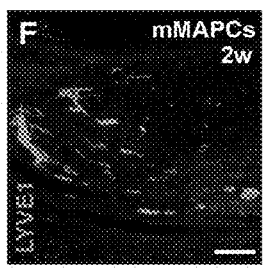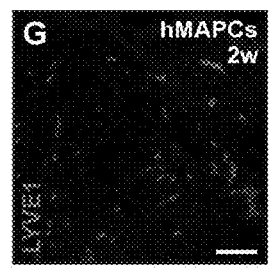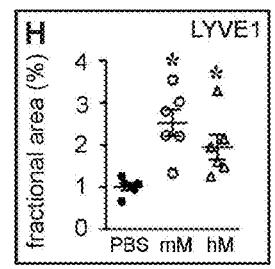
Fig. 8E  Fig. 8F  Fig. 8G  Fig. 8H
Fig. 8I

SEQUENCE LISTING

<160> NUMBER OF SEQ ID NOS: 28

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
cgcgtgggtt tcttctctgc                                              20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gggctgtgct gtcatggtca                                              20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gccagtgttg ttctgggttt                                              20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
agaggtgcct tgccagtaga                                              20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ctgctttcca gtgttgacga                                              20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
aatgcccatc tcctccttct                                              20

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tggccagagg catggagt                                                 18

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tcgcaaatct tcaccacatg g                                             21

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gaaacatccc tcacctgcat                                               20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tggccttttc tctcttccaa                                               20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
aaggagcagg acctggaagt                                               20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gcgtgtatgt gaggatgtgg                                               20

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ccgcatcttc ttgtgcagt                                                19

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gaatttgccg tgagtggagt                                               20

<210> SEQ ID NO 15
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cagtactgaa gagctgtcta taaccagag                                     29

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tctgagcaac ttccaggaat ctc                                           23

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tgctcttcgt tttgggaagc                                               20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tcgctggttc ctggagtcac                                               20

```
<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
aggacgctga tcccttgcta                                                    20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gcactttgat ggttccagcc                                                    20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tttggatgag cagtgtgagc                                                    20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
cggcacgtag gtgatttctt                                                    20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
acacctgcct catgctcagc                                                    20

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
agcagtacag agatggttgc attc                                               24

<210> SEQ ID NO 25
```

```
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
tgctggtatg gagtataggc agtg                                          24

<210> SEQ ID NO 26
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ccggaatgca cgcagg                                                   16

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
tggtatcgtg gaaggactca tgac                                          24

<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
atgccagtga gcttcccgtt cagc                                          24
```

STEM CELLS FOR WOUND HEALING

SEQUENCE LISTING

The instant application contains a Sequence Listing which has been submitted electronically in ASCII format and is hereby incorporated by reference in its entirety. Said ASCII copy, created on Feb. 12, 2021, is named ATY-0029US_SL.txt and is 6,609 bytes in size.

FIELD OF THE INVENTION

The present invention provides a method for treating wounds by applying cells as described in this application. In one aspect the method provides treatment for cutaneous wounds. In general embodiments the cells are delivered to the wound without being attached to a functionalized substrate in the delivery vehicle.

BACKGROUND OF THE INVENTION

The skin is the body's first line of defense from injury and microorganisms and plays an important role in the physical function. Traumatic injuries, burns and chronic ulcers may cause severe damage of the skin, which affects the primary immune function of the skin barrier and then may be accompanied with systemic risk.

Optimum healing of a cutaneous wound requires the processes of inflammation, re-epithelialization, granulation tissue formation, angiogenesis, wound contraction and extracellular matrix (ECM) reconstruction, which contribute to skin tissue regeneration after traumatic injury.

Wound healing is an intricate process in which the skin tissue repairs itself after injury. In normal skin, the epidermis (surface layer) and dermis (deeper layer) form a protective barrier against the external environment. When the barrier is broken, an orchestrated cascade of biochemical events is quickly set into motion to repair the damage. This process is divided into predictable phases: blood clotting (hemostasis), inflammation, the growth of new tissue (proliferation), and the remodeling of tissue (maturation). Sometimes blood clotting is considered to be part of the inflammation stage instead of its own stage.

Hemostasis (blood clotting): Within the first few minutes of injury, platelets in the blood begin to stick to the injured site. This activates the platelets, causing a few things to happen. They change into an amorphous shape, more suitable for clotting, and they release chemical signals to promote clotting. This results in the activation of fibrin, which forms a mesh and acts as "glue" to bind platelets to each other. This makes a clot that serves to plug the break in the blood vessel, slowing/preventing further bleeding.

Inflammation: During this phase, damaged and dead cells are cleared out, along with bacteria and other pathogens or debris. This happens through the process of phagocytosis, where white blood cells "eat" debris by engulfing it. Platelet-derived growth factors are released into the wound that cause the migration and division of cells during the proliferative phase.

Proliferation (growth of new tissue): In this phase, (lymph)angiogenesis, collagen deposition, granulation tissue formation, epithelialization, and wound contraction occur. In angiogenesis, vascular endothelial cells form new blood vessels, while lymphatic endothelial cells contribute to the formation of new lymphatic vessels. In fibroplasias and granulation tissue formation, fibroblasts grow and form a new, provisional extracellular matrix (ECM) by excreting collagen and fibronectin. Concurrently, restoration of the epidermis occurs, in which epithelial cells proliferate and "crawl" atop the wound bed, providing cover for the new tissue. In wound contraction, myofibroblasts decrease the size of the wound by gripping the wound edges and contracting using a mechanism that resembles that in smooth muscle cells. When the cells' roles are close to complete, unneeded cells undergo apoptosis.

Maturation (remodeling): During maturation and remodeling, collagen is realigned along tension lines, and cells that are no longer needed are removed by programmed cell death, or apoptosis.

The wound healing process is not only complex but also fragile, and it is susceptible to interruption or failure leading to the formation of non-healing chronic wounds. Factors that contribute to non-healing chronic wounds are diabetes, venous or arterial disease, infection, and metabolic deficiencies of old age.

Wounds can result from a variety of causes, including for example trauma, disease, action of micro-organisms and exposure to foreign materials. Wound healing it not only important to achieve wound closure, but is also important to restore tissue functionality and to provide a barrier function against infection. Delayed wound healing is a significant contributor to morbidity in subjects. In some situations, the wound healing process is dysfunctional, leading to the development of chronic wounds. Chronic wounds have major impacts on the physical and mental health, productivity, morbidity, mortality and cost of care for affected individuals.

Chronic wounds are defined as wounds that fail to heal after 3 months. Venous stasis ulcers, diabetic ulcers, pressure ulcers, and ischemic ulcers are the most common chronic wounds. Many of the dressing options that attempt to heal venous stasis ulcers are a variation on the classic paste compression bandage, Unna's boot. These wounds can sometimes have large amounts of exudates that require frequent debridement. Alginates, foams and other absorptive can be used in this situation. Because chronic wounds heal by slightly different mechanisms than those of acute wounds, experimentation with growth factors is being investigated. Regranex® and Procuren® (Curative Health Services, Inc., Hauppauge, N.Y.) are the only medications approved by the U.S. Food and Drug Administration (FDA).

Wound care encourages and speeds wound healing via cleaning and protection from reinjury or infection. Depending on each patient's needs, it can range from the simplest first aid to entire nursing specialties such as wound, ostomy, and continence nursing and burn center care.

Each year, over 1.5 million skin wounds are due to burns and over 1 million skin wounds are due to skin cancer. Each year, skin wounds result in about 75,000 inpatient cases and 12,000 deaths, and in 2005, about $3.3 billion dollars were spent on wound care.

In the body, skin wound healing involves fibroblast secretion of a provisional matrix, a process that usually begins 7 days post-injury. However, the currently available tissue engineered skin substitutes are decellularized human skin, such as Alloderm®, which are used for humans in cases of chronic skin wounds (e.g., due to diabetes, vasculitis, malnutrition, infection), acute skin wounds (e.g., burns, skin cancer), skin malformation, etc. Such decellularized skin substitutes lack adnexal structures (e.g., sebaceous glands, hair follicles, melanocytes), a rete ridge pattern at the epidermal-dermal junction, and other vital living components that promote wound healing. Furthermore, high risk of infection remains in heterologous transplantation of the currently available skin substitutes.

Since the regeneration of both dermal and epidermal skin layers are critical for successful wound healing with limited scar formation and infection, new models are needed that are "true" skin substitutes.

The most commonly used conventional modality to assist in wound healing involves the use of wound dressings. A variety of different types of dressings are used to assist with wound healing. Some treatments have also utilized the provision of minerals and vitamins to assist with wound healing. However, these types of treatment modalities have met with little success. As such, current clinical approached used to promote wound healing include protection of the wound bed from mechanical trauma, control of surface microbial burden through antibiotics, antiseptics and other antimicrobial compounds, and the use of some types of growth factors. However, these approaches all have a variety of disadvantages.

The healing of wounds is an example where the delivery of cells has therapeutic potential. Despite advances in the understanding of the principles underlying the wound healing process, the therapeutic options for wound treatment still remain limited. Cell delivery strategies provide a potential therapeutic avenue.

While the delivery of cells has therapeutic potential, the use of cell delivery still remains limited for a number of reasons. For example, considerations such as how cells should be delivered, substrate selection, attachment of cells, efficiency of cell transfer and/or the ability of cells to retain their therapeutic properties are important to therapeutic outcome.

Researchers have used stem cells from different sources to treat traumatic skin injury, to accelerate the regeneration and reconstruction of the skin defects (Yaojiong et al., Stem Cells, 25(10): 2648-59, 2007). However, there are still problems with stem cell therapies, such as limited sources of stem cells. Accordingly, there is a continuing need to identify new cells and/or means for delivery of cells, for therapeutic purposes.

Despite these advances in the art, a need exists in the art for new and better methods and devices for restoring the natural process of wound healing at a lesion, the repair of which requires tissue remodeling and restoration.

BRIEF SUMMARY OF THE INVENTION

The present invention provides a method for treating certain wounds by applying to those wounds certain cells as described herein for healing the wound.

Routes of delivery include, but are not limited to, topical administration forms. Examples of forms of topical administration include delivery by way of a gel, an ointment, a cream, a lotion, a foam, an emulsion, a suspension, a spray, an aerosol, a solution, a liquid, a powder, a semi-solid, a gel, a jelly; a solid, a paste, a tincture, a liniment, a degradable carrier, a pharmaceutically acceptable carrier, a fluid, a reservoir, a liquid, a gel, an implant, such as a PVA-loaded sponge, collagen gel solution, membrane preparation, such as placental membranes, amniotic membranes, collagen sponge, fibrin or other protein glue, in fluid communication suspension in a pharmaceutically acceptable carrier, for example, saline, sugars, for example, dextrose, isotonic aqueous diluent solution, powder, a skin substitute, such as a protein, e.g., fibrin, or membrane preparation, decellularized tissue preparations, for example, decellularized skin preparations, a scaffold, including hydrogel, Matrigel, spongastan, fibronectin, PLGA, collagen gel, fibrin spray, or other protein spray or membrane spray.

Administration may also be by means of a patch, bandage, gauze, or dressing, wherein the bandage, patch, gauze, or dressing does not contain a functionalized substrate to which the cells are attached and from which they migrate to the wound, such as, chemical modification with an alkyl group, such as, an alkylamine group. Other forms of topical delivery are contemplated.

Delivery may also be intradermal or subcutaneous with any of the forms mentioned above with respect to topical delivery.

The cells may be delivered by local injection to the wound in any of the appropriate carriers, such as those mentioned above, with respect to topical administration.

The cells may be implanted in a wound with any of the above delivery vehicles as appropriate, for example, in a PVA-loaded sponge.

In certain embodiments the cells are not delivered in a bandage, gauze, patch, or dressing. In more specific embodiments the cells are not delivered in any of these vehicles wherein the vehicles comprise a functionalized substrate. In more specific embodiments the vehicles do not include a functionalized substrate that is a chemical modification, such as with an alkyl group, such as an alkylamine group.

However, the cells may be delivered by means of functionalized substrates that do not include chemical modifications with alkyl groups. Thus, the cells could be delivered by way of substrates functionalized with protein or other biological material that is derived from tissues or mimic those found in tissues such as membrane preparations, including, but not limited to, amniotic membrane.

In specific excluded embodiments, the cells are not delivered by means of a device (such as bandage, gauze, dressing, or patch) that is chemically modified with an alkyl group and, particularly, an alkylamine group.

In one aspect, the cells are delivered to the wound but not in a cell-laden patch, bandage, or dressing. In a specific embodiment the cells are not attached to a functionalized substrate.

The cells described herein may be administered to the wound in a pharmaceutically acceptable carrier. Pharmaceutically-acceptable carriers include, but are not limited to, water, glucose, glycerol, saline, ethanol, liquid oil, such as palmitates, polyethylene glycol, tween, and SDS, among others.

In certain embodiments, the pharmaceutical composition is suitable for delivery to a subject by one or more of intravenous administration, by aerosolized administration, by parenteral administration, by implant, by subcutaneous injection, intraarticularly, rectally, intranasally, intraocularly, vaginally, or transdermally.

In certain embodiments, the pharmaceutical composition comprises other compounds that enhance, stabilize or maintain the activity of the cells for delivery and/or their delivery or transfer.

In certain embodiments, it may be desirable to administer the pharmaceutical composition parenterally (such as directly into the joint space) or intraperitoneally. For example, solutions or suspensions can be prepared in water suitably mixed with a surfactant such as hydroxy-propylcellulose. Dispersions can also be prepared in glycerol, liquid polyethylene glycols and mixtures thereof in oils.

In certain embodiments, it may be desirable to administer the composition by injection. Forms suitable for injectable use include sterile aqueous solutions or dispersions and sterile powders for the extemporaneous preparation of sterile injectable solutions or dispersions. A carrier can be a solvent or dispersion medium containing, for example, water, ethanol, polyol (e.g., glycerol, propylene glycol and liquid polyethylene glycol), suitable mixtures thereof, and vegetable oils.

In certain embodiments, it may be desirable to administer the composition intravenously. Compositions containing the composition described herein suitable for intravenous administration may be formulated by a skilled person.

In certain embodiments the composition may be administered by injection, e.g., as a cell suspension, in a foam or paste, i.e., by 3D support consisting of polymers or other molecules, meshes, or micro-carriers.

In one aspect, the present invention provides a method for treating a wound to the skin, which comprises administering to the skin wound a composition comprising stem cells. The wound to the skin can be limited or extensive. It can be confined to the epidermis or can also involve the dermis, fatty layer, muscle, and even bone. Thus, the wound can extend to cutaneous and subcutaneous tissues.

The wound may be selected from the group consisting of lacerations, scrapes, burns, incisions, punctures, wounds caused by a projectile and epidermal wounds, skin wound, chronic wound, acute wound, external wound, internal wound, congenital wound, ulcer, pressure ulcer, diabetic ulcer, tunnel wound, wound caused during or as an adjunct to a surgical procedure, venous skin ulcer, and avascular necrosis.

In one embodiment the wounds are of a class that arise because of insufficient blood and/or lymphatic circulation. Within this class, species include, in particular, chronic wounds that result from this insufficient circulation, such as, diabetic ulcers, venous skin ulcers, and avascular necrosis. In particular cutaneous wounds may be treated by the methods of the invention. It is understood, however, that these cutaneous wounds, particularly when chronic, can affect the subcutaneous layers and may actually expose deeper muscle and even bone tissue. This can be the case with diabetic foot ulcers, venous leg ulcers and burns.

The term "wound" includes, for example, an injury to a tissue, including open wounds, delayed or difficult to heal wounds, and chronic wounds. Examples of wounds may include both open and closed wounds. The term "wound" also includes, for example, injuries to the skin and subcutaneous tissue and injuries initiated in different ways and with varying characteristics.

In certain embodiments, the wound comprises an external wound. In certain embodiments, the wound comprises an open wound. In certain embodiments, the wound comprises a chronic wound. In certain embodiments, the wound comprises a chronic wound or an ulcer.

For external wounds, typically these wounds are classified into one of four grades depending on the depth of the wound: i) Grade I wounds limited to the epithelium; ii) Grade II wounds extending into the dermis; iii) Grade III wounds extending into the subcutaneous tissue; and iv) Grade IV (or full-thickness wounds) wounds wherein bones are exposed.

The invention is directed to methods of promoting cutaneous wound healing, including, administering to a patient an effective amount of stem cells, thereby resulting in at least one of accelerated wound closure, rapid re-epithelialization, improved (lymph)angiogenesis and improved tissue remodeling, relative to untreated controls.

Positive results in wound healing include, but are not limited to, enhanced epithelialization, granulation tissue formation and angiogenesis, accelerated wound closure, deposition of granulation tissue, increased wound bursting strength with increased collagen content, increased wound tensile strength, reduced scarring, and reduced wound size.

Wounds include cutaneous wounds. They also include wounds that reach all layers of the dermis, including, the subcutaneous and fat layers, i.e., the underlying tissues as well. The invention applies to chronic wounds, wounds that result from obesity or diabetes, non-healing diabetic wounds, diabetic wounds in general, diabetic foot ulcers, burns, neuropathic foot ulcers, diabetic neuropathic ulcers, and chronic cutaneous ulcers. Wounds may result in the cutaneous and subcutaneous tissues by underlying causes, such as, lack of sufficient blood circulation or lymphatic circulation. Methods of the present invention and compositions of the present invention, thus, promote re-epithelialization, i.e., wound closure whether full or partial.

In accordance with a further aspect of the present invention, there is provided a method of promoting wound healing in a subject. The method comprises administering to the subject stem cells in an amount effective to promote wound healing in the subject. In one embodiment the subject is human. However, the invention includes veterinary subjects (e.g., dogs, cats, pigs, horses, etc.).

There are three phases of normal wound healing including, bleeding and coagulation, acute inflammation, cell migration, proliferation, differentiation, angiogenesis, re-epithelialization, and synthesis and remodeling of extracellular matrix. All of these events occur in three overlapping phases, specifically, inflammatory, proliferative, and remodeling. The cells in the present application can be used in one or more of these phases. They need not be used, but may be used, in all three of these phases.

Chronic wounds are those that fail to progress through the three normal stages of healing. This results in tissue injury that is not repaired within the typical time period. These may result from various underlying disorders that include, but are not limited to, diabetes, pressure, vascular insufficiency, burns, and vasculitis (Borue, et al.; *Am J Pathol* (2004) 165:1767-1772). The cells in the present application can be used in one or more of these stages.

The stem cells are administered to the animal in an amount effective to promote wound healing in the animal. The animal may be a mammal, and the mammal may be a primate, including human and non-human primates. In general, the stem cells are administered in an amount of from about $1\times10^5$ cells/kg to about $1\times10^7$ cells/kg, preferably from about $1\times10^6$ cells/kg to about $5\times10^6$ cells/kg. In a specific embodiment $2-4\times10^7$ cells/kg are administered. The exact amount of stem cells to be administered is dependent upon a variety of factors, including the age, weight, and sex of the patient, and the extent and severity of the wound being treated.

The stem cells may be administered in conjunction with an acceptable pharmaceutical carrier. The stem cells may be administered systemically. The stem cells may be administered directly to a wound, a fluid or reservoir containing the stem cells such as PBS, buffered salts, cell media, Plasma-Lyte.

In some embodiments the cells are delivered with additional factors. These include, but are not limited to, one or more of antiflammatory and antimicrobial factors, including defensins, N-Gal, IL-1RA, angiogenic factors, such as, VEGF, bFGF, PDGF, epithelial cell stimulatory proteins, including KGF and EGF and antiscarring proteins TGFβ3, IFNα2, and HGF.

The cells to which the invention is directed may express pluripotency markers, such as oct4. They may also express markers associated with extended replicative capacity, such as telomerase. Other characteristics of pluripotency can include the ability to differentiate into cell types of more than one germ layer, such as two or three of ectodermal, endodermal, and mesodermal embryonic germ layers. Such cells may or may not be immortalized or transformed in culture. The cells may be highly expanded without being transformed and also maintain a normal karyotype. For example, in one embodiment, the non-embryonic stem, non-germ cells may have undergone at least 10-40 cell doublings in culture, such as 50, 60, or more, wherein the cells are not transformed and have a normal karyotype. The cells may differentiate into at least one cell type of each of two of the endodermal, ectodermal, and mesodermal embryonic lineages and may include differentiation into all three. Further, the cells may not be tumorigenic, such as, not producing teratomas. If cells are transformed or tumorigenic, and it is desirable to use them for infusion, such cells may be disabled so they cannot form tumors in vivo, as by treatment that prevents cell proliferation into tumors. Such treatments are well known in the art.

Cells include, but are not limited to, the following numbered embodiments:

1. Isolated expanded non-embryonic stem, non-germ cells, the cells having undergone at least 10-40 cell doublings in culture, wherein the cells express oct4, are not transformed, and have a normal karyotype.

2. The non-embryonic stem, non-germ cells of 1 above that further express one or more of telomerase, rex-1, rox-1, or sox-2.

3. The non-embryonic stem, non-germ cells of 1 above that can differentiate into at least one cell type of at least two of the endodermal, ectodermal, and mesodermal embryonic lineages.

4. The non-embryonic stem, non-germ cells of 3 above that further express one or more of telomerase, rex-1, rox-1, or sox-2.

5. The non-embryonic stem, non-germ cells of 3 above that can differentiate into at least one cell type of each of the endodermal, ectodermal, and mesodermal embryonic lineages.

6. The non-embryonic stem, non-germ cells of 5 above that further express one or more of telomerase, rex-1, rox-1, or sox-2.

7. Isolated expanded non-embryonic stem, non-germ cells that are obtained by culture of non-embryonic, non-germ tissue, the cells having undergone at least 40 cell doublings in culture, wherein the cells are not transformed and have a normal karyotype.

8. The non-embryonic stem, non-germ cells of 7 above that express one or more of oct4, telomerase, rex-1, rox-1, or sox-2.

9. The non-embryonic stem, non-germ cells of 7 above that can differentiate into at least one cell type of at least two of the endodermal, ectodermal, and mesodermal embryonic lineages.

10. The non-embryonic stem, non-germ cells of 9 above that express one or more of oct4, telomerase, rex-1, rox-1, or sox-2.

11. The non-embryonic stem, non-germ cells of 9 above that can differentiate into at least one cell type of each of the endodermal, ectodermal, and mesodermal embryonic lineages.

12. The non-embryonic stem, non-germ cells of 11 above that express one or more of oct4, telomerase, rex-1, rox-1, or sox-2.

13. Isolated expanded non-embryonic stem, non-germ cells, the cells having undergone at least 10-40 cell doublings in culture, wherein the cells express telomerase, are not transformed, and have a normal karyotype.

14. The non-embryonic stem, non-germ cells of 13 above that further express one or more of oct4, rex-1, rox-1, or sox-2.

15. The non-embryonic stem, non-germ cells of 13 above that can differentiate into at least one cell type of at least two of the endodermal, ectodermal, and mesodermal embryonic lineages.

16. The non-embryonic stem, non-germ cells of 15 above that further express one or more of oct4, rex-1, rox-1, or sox-2.

17. The non-embryonic stem, non-germ cells of 15 above that can differentiate into at least one cell type of each of the endodermal, ectodermal, and mesodermal embryonic lineages.

18. The non-embryonic stem, non-germ cells of 17 above that further express one or more of oct4, rex-1, rox-1, or sox-2.

19. Isolated expanded non-embryonic stem, non-germ cells that can differentiate into at least one cell type of at least two of the endodermal, ectodermal, and mesodermal embryonic lineages, said cells having undergone at least 10-40 cell doublings in culture.

20. The non-embryonic stem, non-germ cells of 19 above that express one or more of oct4, telomerase, rex-1, rox-1, or sox-2.

21. The non-embryonic stem, non-germ cells of 19 above that can differentiate into at least one cell type of each of the endodermal, ectodermal, and mesodermal embryonic lineages.

22. The non-embryonic stem, non-germ cells of 21 above that express one or more of oct4, telomerase, rex-1, rox-1, or sox-2.

The cells described above can be prepared from any desirable tissue source, including, but not limited to, bone marrow, umbilical cord blood, umbilical cord matrix, peripheral blood, placenta, placental blood, muscle, brain, kidney, and other solid organs. They can also be derived from excreted fluids, such as urine and menstrual blood.

In one embodiment, the cells are derived from human tissue.

In specific embodiments the wound contains epithelial damage.

In certain embodiments the cells themselves need not be delivered. The therapeutic effects may be achieved by factors that are secreted by the cells. For example, when the cells are cultured the beneficial factors may be secreted into the cell culture medium. Therefore, the medium, itself, may be used in the various embodiments disclosed in the application. Alternatively, extracts of the conditioned medium may be used, the extracts containing the beneficial factors by which the cells provide a therapeutic result in wound healing as described in this application. Thus wherever cells may be delivered, the conditioned medium or extracts thereof may be substituted or added.

BRIEF DESCRIPTION OF THE FIGURES

FIGS. 1A and B; Diagram representing expression of general (right) and lymphatic-specific (left) endothelial cell (EC) markers, shown as % versus universal mouse RNA in undifferentiated mMAPCs (A) or versus universal human RNA in undifferentiated hMAPCs (d0, white), at 14 (d14, gray) and 21 (d21, black) days of differentiation. Data represent mean±SEM of 5-6 independent differentiations. *P<0.05 versus d0 by Kruskal-Wallis test with Dunn's post-hoc test. FIG. 1C; FACS histogram (representative of n=3) showing LYVE1 protein expression (full line) versus isotype control (dashed line) in mMAPCs at d14. APC: allophycocyanine. FIG. 1D; Diagram representing LYVE1 expression, shown as fold-increase versus undifferentiated hMAPCs (d0, white), or at d9 in the presence of VEGF-A (light gray), VEGF-C(dark gray) or a combination (black). Data represent mean±SEM of n=3. *P<0.05 versus d0 by 1-way ANOVA with Tuckey's post-hoc test. FIGS. 1E-G; Representative images of human lymphatic EC (hLEC) spheroids exposed to LEC media (E; 'L') or conditioned media from mMAPCs ('mCM'; F), and corresponding quantification (G; data represent mean±SEM of n=4; *P<0.05 versus 'L' by Mann-Whitney-U test). FIG. 1H; Diagram representing the effect of mouse ('mCM') or human ('hCM') MAPC-CM on LEC proliferation, expressed as % versus LEC media. Data represent mean±SEM of n=3-6. *P<0.05 versus TEC' by Mann-Whitney-U test. FIGS. 1I-M; Representative images of LECs migrated across the membrane of a transwell (revealed by Wright-Giemsa staining) in the presence of non-conditioned mMAPC media (NCM; J), mMAPC-CM (K), non-conditioned hMAPC media (NCM; L) or hMAPC-CM (M) and the corresponding quantification (I; data represent mean±SEM of n=4; *P<0.05 versus corresponding NCM condition by Mann-Whitney-U test). Scale bars: 50 μm (E,F); 100 μm (J-M).

FIG. 2A; Wound width in mice treated with PBS (open circles) or mMAPCs (filled circles). Data represent mean±SEM. n=5; *P<0.05 versus PBS by repeated measures ANOVA and Fisher post-hoc test.

FIG. 2P; Image of a wound cross-section of a mouse transplanted with hMAPCs 10d earlier revealing occasional co-localization (arrowheads) of hVimentin (green) with LYVE1 (red). Hematoxylin and DAPI were used to reveal nuclei in C,D,I-L and E,F,M,N, respectively. Scale bars: 10 μm (H,P); 100 μm (E,F); 150 μm (K,L); 400 μm (C,D,I,J,M,N); 2 mm (B).

FIG. 3A; Image displaying the skin flap model. R1/R2 indicate the areas from which images in panel B-D are shown. Arrows/A' indicate injection spots of fluorescently-labeled dextran for lymphangiography or MAPCs/PBS, respectively, and arrowheads show the area through which blood supply to the skin flap is preserved. FIGS. 3B-D; Representative merged pictures of brightfield/fluorescent images 15 min after injection of dextran (FITC-labeled in B,D or Rhodamin-B-labeled in C) of regions R1 (left; and enlarged image of the corresponding inset (i; middle)) and R2 (right) of mice injected 2w earlier with PBS (B), mMAPCs (C) or hMAPCs (D). Arrowheads indicate filled afferent lymphatic vessels. LN: lymph node. Dashed lines in R1/R2 delineate border of the opened skin or the flap border, respectively. Scale bars: 100 μm (B;i1, C;i2+R2, D;i3); 250 μm (B;R1+R2, C;R1, D;R1+R2); and 500 μm (A).

FIGS. 4A-4L: FIGS. 4A-D; Representative pictures of Flt4-stained (brown) skin wound cross-sections (around the location of dextran injection) from mice treated with PBS (A), mMAPCs ('mM'; B) or hMAPCs ('hM'; C), and corresponding quantification (D; data represent mean±SEM. *P<0.05 versus PBS by Kruskal-Wallis with Dunn's post-hoc test; n=6). FIGS. 4E-H; Representative pictures of skin wound cross-sections (around the location of dextran injection) from mice treated with PBS (E), mMAPCs ('mM'; F) or hMAPCs ('hM'; G) revealing functional (dextran-perfused) lymphatic vessels (green or red) in cell-treated mice, and corresponding quantification (H; data represent mean±SEM. *P<0.05 versus PBS by Kruskal-Wallis with Dunn's post-hoc test; n=5-10). Inset (i1) in E shows the corresponding region stained for Prox1 (red). Note the diffuse fluorescence signal in E representing FITC-dextran that failed to be taken up by lymphatic vessels. FIG. 4I; Merged brightfield/fluorescent image of the wound area of a mouse transplanted with eGFP$^+$ mMAPCs (injection spots indicated by arrowheads) 2w earlier. FIG. 4J; Merged green/red fluorescent images of the wound area of a mouse transplanted with eGFP$^+$ mMAPCs (arrow) 4w earlier. Note the Rhodamin-dextran-filled lymphatic vessels (red; arrowheads) in the vicinity of the transplanted cells. FIG. 4K; Cross-section through the area around the wound, revealing transplanted eGFP$^+$ mMAPCs adjacent to functional (Rhodamin-dextran-filled, red; lumen indicated by asterisks) lymphatic vessels. FIG. 4L; High power magnification of the wound area transplanted with eGFP$^+$ mMAPCs 2w earlier revealing that occasionally these cells become part of the endothelial lining (arrowheads) of functional (Rhodamin-dextran-filled, in red) lymphatic vessels. Hematoxylin and DAPI were used to reveal nuclei in A-C, and E-G,K, respectively. Scale bars: 25 μm (L); 50 μm (E-G); 100 μm (A-C,J,K); 500 μm (I).

FIG. 5A-5G: FIG. 5A; Merged brightfield/fluorescent image of the right axillary region of a mouse transplanted with an eGFP$^+$ lymph node (LN; arrowhead) and treated with Matrigel® containing hMAPCs 16w earlier. The area covered with solidified Matrigel® and the open skin border are indicated by a dashed and full white lines, respectively. FIG. 5B; Diagram representing the extent of edema in the right upper limb (determined by MRI and shown as right/left ratio in AU) in mice treated with Matrigel® containing PBS or hMAPCs 4w or 16w after LN transplantation. *P<0.05 versus w4 by unpaired Student's t-test (n=4-9). FIGS. 5C and D; Representative T$_2$-weighted MR images of the antebrachial regions of mice treated with Matrigel® containing PBS (C) or hMAPCs (D), recorded 16w after LN transplantation. Hyperintense areas (arrows) indicate accumulation of fluid due to edema. L: left; R: right.

FIGS. 5E and F; Merged brightfield/fluorescent image of the right axillary region of a mouse transplanted with an eGFP$^+$ LN (arrowhead) and treated with Matrigel® containing PBS (E) or hMAPCs (F) 16w earlier. Inset (i1) zooms in on the boxed area in F. Note the significantly improved drainage of the Rhodamin-labeled lectin (red) in hMAPC-treated mice recorded 15 min after injection (injection spot indicated by arrow). The border of the opened skin is indicated by white lines. FIG. 5G; Merged brightfield/fluorescent image zooming in on an eGFP$^+$ LN (green) transplanted in a mouse treated with Matrigel® containing hMAPCs 16w earlier, revealing drainage of the Rhodamin-labeled lectin (red) into the LN. Arrowheads indicate afferent lymph vessel. Scale bars: 200 µm (G); 3 mm (A,E,F).

FIGS. 6A-6N: FIGS. 6A-C; Brightfield images of the blood vessel network leading up to the transplanted lymph node (LN) of mice treated with Matrigel® containing PBS (A) or hMAPCs ('hM'; B) 16w earlier, and corresponding quantification (C; data represent mean±SEM. *P<0.05 versus PBS by Mann-Whitney-U test; n=6). FIG. 6D; Merged brightfield/fluorescent image of an eGFP$^+$ LN transplanted in a mouse treated with Matrigel® containing hMAPCs 16w earlier revealing that the LN is irrigated by numerous blood vessels. FIGS. 6E and F; Merged brightfield/fluorescent images zooming in on a DsRed$^+$ LN transplanted in mice treated with Matrigel® containing hMAPCs 8w earlier revealing extensive branching of the LN vascular network. Inset (i1) corresponds to the boxed area in F. FIG. 6G; Merged IF image of a Prox1/eGFP-stained section in a mouse treated with Matrigel®+hMAPCs 16w earlier revealing that part of the branches are lymphatic (Prox1$^+$, arrowheads). Inset (i2) corresponds to the boxed area in G. FIGS. 6H-J; LYVE1-stained (red) cross-sections of PBS (H) or hMAPC-treated ('hM'; I) mice in the area around the sutures at 8w after LN transplantation and corresponding quantification (J; data represent mean±SEM. *P<0.05 versus PBS by Student's t-test; n=5-8). FIGS. 6K-M; Fluorescence images of the area around the transplanted eGFP$^+$ LN (lined by a dashed line in K; adjacent section stained for Prox1 in green is shown in L; Prox1/smooth muscle α-actin (αSMA in red, indicated by arrowheads; double staining in M zooms in on the boxed area in K,L; and FIG. 6N represents the same area on an adjacent cross-section stained for LYVE1 in red) revealing Prox1αSMA$^+$ LYVE1 draining lymphatic collector vessels in mice 16w earlier treated with Matrigel® containing hMAPCs. Asterisks in L-N indicate lymph (which artifactually fluoresces upon exposure to tyramide-based amplification). White arrows in A,B,E-L indicate the sutures used to fix the transplanted LN. Scale bars: 20 µm (M,N); 50 µm (G,K,L); 100 µm (D); 150 µm (F;i1); 200 µm (E,H,I); 500 µm (F); 1 mm (A,B).

FIG. 7A; Diagram representing wound length (in mm) in mice treated with PBS (n=5: open circles) or mMAPCs (n=5; filled circles) until 10d after wounding. Data represent mean±SEM. *P<0.05 versus PBS by repeated measures ANOVA with Fisher post-hoc test. FIGS. 7B and C; Representative brightfield pictures of linear wounds on the back of mice treated with PBS (B) or murine (m)MAPCs (C) 10d after wounding. FIGS. 7D and E; Representative pictures of cross-sections of 10d-old wounds from mice treated with PBS (D) or mMAPCs (E) stained with H&E. Note the significantly smaller wound gap (the edges of which are indicated by arrowheads) in mMAPC-treated mice. FIG. 7F; Merged picture of red and green fluorescent image of a wound cross-section revealing no co-localization of CD45 (in green) with LYVE1 (in red). FIG. 7G; Merged picture of brightfield/fluorescent image of the wound bed 24 h after seeding of eGFP-labeled hMAPCs revealing homogenous distribution of eGFP+hMAPCs across the wound area. FIG. 7H; Image of a vimentin-stained (green) wound cross-section of a mouse transplanted with hMAPCs 10d earlier revealing persistence of large patches of hMAPCs homogenously distributed across the wound bed. The dermo-epidermal junction is indicated by a dashed line. DAPI was used as nuclear counterstain in H. Scale bars: 20 µm in F; 100 µm in H; 300 µm in D,E; 1 mm in G; and 2 mm in B,C.

FIGS. 8A-8L-FIGS. 8A-D; Representative pictures of cross-sections of the skin wound (around the location of transplantation indicated by 'X' in FIG. 3A) from mice treated with PBS (A), mMAPCs ('mM'; B) or hMAPCs ('hM'; C) stained for CD31 (in brown), and corresponding quantification (D; data represent mean±SEM. *P<0.05 versus PBS by Kruskal-Wallis test with Dunn's post-hoc test; n=5). FIGS. 8E-H; Representative pictures of cross-sections of the skin wound (around the location of dextran injection indicated by arrow in FIG. 3A) from mice treated with PBS (E), mMAPCs ('mM'; F) or hMAPCs ('hM'; G) stained for LYVE1 (red in E,G; green in F), and corresponding quantification (H; data represent mean±SEM. *P<0.05 versus PBS by Kruskal-Wallis test with Dunn's post-hoc test; n=6). FIG. 8I; Merged picture of green (FITC-labeled dextran), red (Prox1) and far-red (smooth muscle cell-α-actin; αSMA) fluorescent microscopic images of the wound area (around the location of transplantation indicated by 'X' in FIG. 3A) of a mouse transplanted with hMAPCs 2w earlier, revealing a functional αSMA-coated (arrowheads) Prox1$^+$ lymphatic (pre-)collector vessel in addition to two small functional Prox1$^+$/αSMA lymphatic capillaries (lined by white dashed lines). The autofluorescent muscle cells of the fascia are lined by a red dashed line. Scale bars: 10 µm in I; and 100 µm in A-C,E-G.

FIGS. 9A and B; T$_2$ maps corresponding to the T$_2$-weighted MR images shown in FIG. 5C,D of the antebrachial regions of mice treated with Matrigel® containing PBS (A) or hMAPCs (B), recorded 16w after LN transplantation. L: left; R: right. FIG. 9C; Merged picture of green and red fluorescent microscopic images of the right axillary region of a mouse transplanted with a DsRed$^+$ LN and treated with Matrigel® containing hMAPCs 8w earlier. Note the afferent lymphatic vessel filled with FITC-labeled lectin (in green), indicated by arrowheads. FIGS. 9D and E; Merged pictures of brightfield and green fluorescent images of the right axillary region of mice transplanted with an eGFP$^+$ LN and treated with Matrigel® containing PBS (D) or hMAPCs (E) 16w earlier, revealing a more elaborate blood vessel network irrigating the transplanted LN of hMAPC-treated mice. FIG. 9F; Merged picture of a red and green fluorescent image of a cross-section of the right axillary region of a mouse transplanted with an eGFP$^+$ LN and treated with hMAPCs 16w earlier, revealing persisting vimentin-stained (in red) hMAPCs surrounding the transplanted LN. FIG. 9G; Merged picture of brightfield and green fluorescent images of the right axillary region of a mouse transplanted with an eGFP$^+$ LN and treated with Matrigel® containing hMAPCs 4w earlier, revealing outward branching of the (lymph)vascular network. FIG. 9H; Merged picture of an eGFP-stained cross-section of the right axillary region of a mouse transplanted with an eGFP$^+$ LN and treated with Matrigel® containing hMAPCs 16w earlier, revealing outward branches of the (lymph)vascular network. Permanent sutures fixing the transplanted LN are indicated by arrows in C-E. LN body is lined by a white dashed line in F-H. DAPI was used to reveal nuclei in F,H. Scale bars: 25 μm in F; 100 μm in H; 150 μm in G; and 250 μm in C-E.

DETAILED DESCRIPTION OF THE INVENTION

Figure 1A:
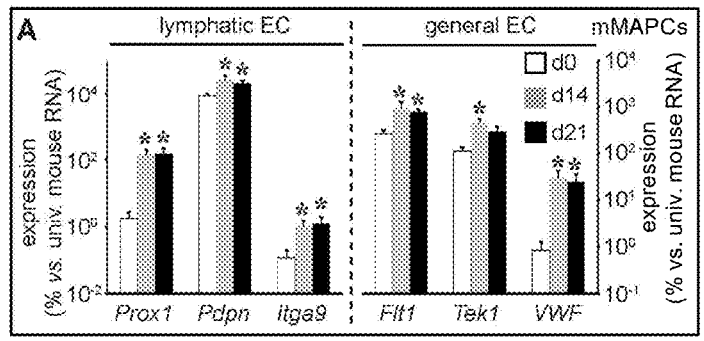
FIGS. 1A-1M.
Figure 1B:
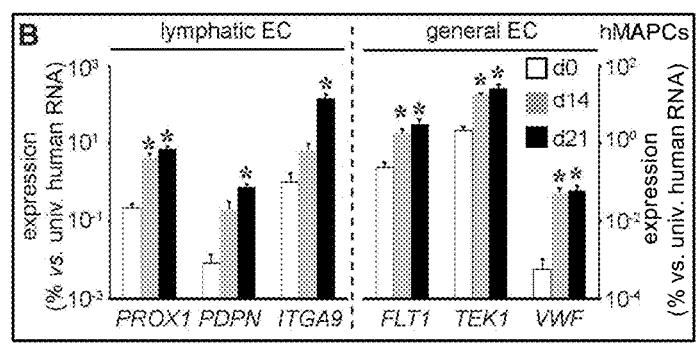

It should be understood that this invention is not limited to the particular methodology, protocols, and reagents, etc., described herein and, as such, may vary. The terminology used herein is for the purpose of describing particular embodiments only, and is not intended to limit the scope of the disclosed invention, which is defined solely by the claims.

The section headings are used herein for organizational purposes only and are not to be construed as in any way limiting the subject matter described.

The methods and techniques of the present application are generally performed according to conventional methods well-known in the art and as described in various general and more specific references that are cited and discussed throughout the present specification unless otherwise indicated. See, e.g., Sambrook et al., *Molecular Cloning: A Laboratory Manual*, 3rd ed., Cold Spring Harbor Laboratory Press, Cold Spring Harbor, N.Y. (2001) and Ausubel et al., *Current Protocols in Molecular Biology*, Greene Publishing Associates (1992), and Harlow and Lane, *Antibodies: A Laboratory Manual*, Cold Spring Harbor Laboratory Press, Cold Spring Harbor, N.Y. (1990).

Definitions

"A" or "an" means herein one or more than one; at least one. Where the plural form is used herein, it generally includes the singular.

The term "bandage" as used in this application is synonymous with the terms "dressing" or "patch" as they refer to a functionalized substrate to which cells are attached. These devices have been referred to as cell-laden bandages, cell-laden patches, and cell-laden dressings. In these embodiments the cells that are attached to the substrate, when applied in operable proximity to the wound, leave the patch, dressing, or bandage and migrate to the wound. In some instances these bandages/patches may be comprised of a coating of plasma polymer. As mentioned this can be comprised of a functionalized substrate to which the cells are attached.

A "clinically-relevant" number of cells refers to a number of cells that is sufficient to effect a clinical response; that is, a prevention, reduction, amelioration, etc. of an undesirable pathological condition in a subject. A particular embodiment pertains to a number of cells that is sufficient to create a master cell bank.

"Co-administer" means to administer in conjunction with one another, together, coordinately, including simultaneous or sequential administration of two or more agents.

"Comprising" means, without other limitation, including the referent, necessarily, without any qualification or exclusion on what else may be included. For example, "a composition comprising x and y" encompasses any composition that contains x and y, no matter what other components may be present in the composition. Likewise, "a method comprising the step of x" encompasses any method in which x is carried out, whether x is the only step in the method or it is only one of the steps, no matter how many other steps there may be and no matter how simple or complex x is in comparison to them. "Comprised of and similar phrases using words of the root "comprise" are used herein as synonyms of "comprising" and have the same meaning.

"Comprised of" is a synonym of "comprising" (see above).

"Conditioned cell culture medium" is a term well-known in the art and refers to medium in which cells have been grown. Herein this means that the cells are grown for a sufficient time to secrete the factors that are effective to achieve any of the results described in this application.

Conditioned cell culture medium refers to medium in which cells have been cultured so as to secrete factors into the medium. For the purposes of the present invention, cells can be grown through a sufficient number of cell divisions so as to produce effective amounts of such factors so that the medium has the effects. Cells are removed from the medium by any of the known methods in the art, including, but not limited to, centrifugation, filtration, immunodepletion (e.g., via tagged antibodies and magnetic columns), and FACS sorting.

"Effective amount" generally means an amount which provides the desired local or systemic effect. For example, an effective amount is an amount sufficient to effectuate a beneficial or desired clinical result. The effective amounts can be provided all at once in a single administration or in fractional amounts that provide the effective amount in several administrations. The precise determination of what would be considered an effective amount may be based on factors individual to each subject, including their size, age, injury, and/or disease or injury being treated, and amount of time since the injury occurred or the disease began. One skilled in the art will be able to determine the effective amount for a given subject based on these considerations which are routine in the art. As used herein, "effective dose" means the same as "effective amount."

"Effective route" generally means a route which provides for delivery of an agent to a desired compartment, system, or location. For example, an effective route is one through which an agent can be administered to provide at the desired site of action an amount of the agent sufficient to effectuate a beneficial or desired clinical result.

Use of the term "includes" is not intended to be limiting.

"Increase" or "increasing" means to induce entirely where there was no pre-existing presence or to increase the degree of.

The term "isolated" refers to a cell or cells which are not associated with one or more cells or one or more cellular components that are associated with the cell or cells in vivo. An "enriched population" means a relative increase in numbers of a desired cell relative to one or more other cell types in vivo or in primary culture.

However, as used herein, the term "isolated" does not indicate the presence of only stem cells. Rather, the term "isolated" indicates that the cells are removed from their natural tissue environment and are present at a higher concentration as compared to the normal tissue environment. Accordingly, an "isolated" cell population may further include cell types in addition to stem cells and may include additional tissue components. This also can be expressed in terms of cell doublings, for example. A cell may have undergone 10, 20, 30, 40 or more doublings in vitro or ex vivo so that it is enriched compared to its original numbers in vivo or in its original tissue environment (e.g., bone marrow, peripheral blood, adipose tissue, etc.).

"MAPC" is an acronym for "multipotent adult progenitor cell." It refers to a cell that is not an embryonic stem cell or germ cell but has some characteristics of these. MAPC can be characterized in a number of alternative descriptions, each of which conferred novelty to the cells when they were discovered. They can, therefore, be characterized by one or more of those descriptions. First, they have extended replicative capacity in culture without being transformed (tumorigenic) and with a normal karyotype. Second, they may give rise to cell progeny of more than one germ layer, such as two or all three germ layers (i.e., endoderm, mesoderm and ectoderm) upon differentiation. Third, although they are not embryonic stem cells or germ cells, they may express markers of these primitive cell types so that MAPCs may express one or more of Oct 3/4 (aka, Oct 3A or Oct 4), rex-1, and rox-1. They may also express one or more of sox-2 and SSEA-4. Fourth, like a stem cell, they may self-renew, that is, have an extended replication capacity without being transformed. This means that these cells express telomerase (i.e., have telomerase activity). Accordingly, the cell type that was designated "MAPC" may be characterized by alternative basic characteristics that describe the cell via some of its novel properties.

The term "adult" in MAPC is non-restrictive. It refers to a non-embryonic somatic cell. MAPCs are karyotypically normal and do not form teratomas or other tumors in vivo. This acronym was first used in U.S. Pat. No. 7,015,037 to describe a pluripotent cell isolated from bone marrow. However, cells with pluripotential markers and/or differentiation potential have been discovered subsequently and, for purposes of this invention, may be equivalent to those cells first designated "MAPC." Descriptions of the MAPC type of cell are provided in the Summary of the Invention above.

MAPC represents a more primitive progenitor cell population than MSC (Verfaillie, C. M., *Trends Cell Biol* 12:502-8 (2002), Jahagirdar, B. N., et al., *Exp Hematol*, 29:543-56 (2001); Reyes, M. and C. M. Verfaillie, *Ann N Y Acad Sci*, 938:231-233 (2001); Jiang, Y. et al., *Exp Hematol*, 30896-904 (2002); and Jiang, Y. et al., *Nature*, 418:41-9. (2002).

"Progenitor cells" are cells produced during differentiation of a stem cell that have some, but not all, of the characteristics of their terminally-differentiated progeny. Defined progenitor cells, such as "cardiac progenitor cells," are committed to a lineage, but not to a specific or terminally differentiated cell type. The term "progenitor" as used in the acronym "MAPC" does not limit these cells to a particular lineage. A progenitor cell can form a progeny cell that is more highly differentiated than the progenitor cell.

Selection could be from cells in a tissue. For example, in this case, cells would be isolated from a desired tissue, expanded in culture, selected for a desired characteristic, and the selected cells further expanded.

"Self-renewal" refers to the ability to produce replicate daughter stem cells having differentiation potential that is identical to those from which they arose. A similar term used in this context is "proliferation."

"Serum-free medium" refers to medium in which serum is not present or, if present, is at levels at which the components of the serum have no effect on the growth or variability of the cells (i.e., are not actually necessary, such as residual or trace amounts).

"Stem cell" means a cell that can undergo self-renewal (i.e., progeny with the same differentiation potential) and also produce progeny cells that are more restricted in differentiation potential.

"Subject" means a vertebrate, such as a mammal, such as a human. Mammals include, but are not limited to, humans, dogs, cats, horses, cows, and pigs.

As used herein, the term "wound" means a breach in the integrity of a tissue, e.g., skin, which can be caused by acute trauma or underlying pathological causes such as the cutaneous and subcutaneous wounds that have been described in this application.

Wounds may be derived from sources including, but not limited to, autoimmune-disease, rejection of transplanted organs, burns, cuts, lacerations, and ulcerations, including skin ulcerations and diabetic ulcerations.

The stem cells may be administered to an animal to repair epithelial damage caused by burns, cuts, lacerations, and ulcerations, including, but not limited to, skin ulcerations and diabetic ulcerations.

Examples of wounds may include both open and closed wounds. In certain embodiments, the wound comprises an external wound. In certain embodiments, the wound comprises an open wound. In certain embodiments, the wound comprises a chronic wound. In certain embodiments, the wound comprises a chronic wound or an ulcer.

In certain embodiments, the composition is suitable for topical application, topical administration or topical delivery to a subject. Topical formulations are as described herein. Other forms of delivery of cells are contemplated.

The dose and frequency of topical administration may be determined by one of skill in the art.

Examples of forms for topical administration include delivery by way of a gel, an ointment, a cream, a lotion, a foam, an emulsion, a suspension, a spray, an aerosol, a solution, a liquid, a powder, a semi-solid, a gel, a jelly, a suppository; a solid, an ointment, a paste, a tincture, a liniment, a patch, or release from a bandage, gauze or dressing. Other forms of topical delivery are contemplated.

Methods for incorporating substrates into products for topical release are known in the art, for example as described in Boateng J. S. et al (2008) "Wound healing dressings and drug delivery systems: a review" *J. Pharm Sci.* 97(8): 2892-2923 and "Delivery System Handbook for Personal Care and Cosmetic Products: Technology" (2005) by Meyer Rosen, published William Andrew Inc, Norwich N.Y.

In certain embodiments, the composition is suitable for delivery to a subject by one or more of intravenous administration, by aerosolized administration, by parenteral administration, by implant, by subcutaneous injection, intraarticularly, rectally, intranasally, intraocularly, vaginally, or transdermally.

In certain embodiments, the composition comprises other compounds that enhance, stabilize or maintain the activity of the cells for delivery and/or their delivery or transfer.

In certain embodiments, it may be desirable to administer the composition by injection. Forms suitable for injectable use include sterile aqueous solutions or dispersions and sterile powders for the extemporaneous preparation of sterile injectable solutions or dispersions. A carrier can be a solvent or dispersion medium containing, for example, water, ethanol, polyol (e.g., glycerol, propylene glycol and liquid polyethylene glycol), suitable mixtures thereof, and vegetable oils.

In certain embodiments, it may be desirable to administer the composition intravenously. Compositions containing the composition described herein suitable for intravenous administration may be formulated by a skilled person.

In certain embodiments, the subject is a human or animal subject. In certain embodiments, the subject is a human subject.

In certain embodiments, the subject is a mammalian subject, a livestock animal (such as a horse, a cow, a sheep, a goat, a pig), a domestic animal (such as a dog or a cat) and other types of animals such as monkeys, rabbits, mice, laboratory animals, birds and fish. Other types of animals are contemplated. Veterinary applications of the present disclosure are contemplated. Use of any of the aforementioned animals as animal models is also contemplated.

The present disclosure provide a method of healing or treating a wound, the method comprising delivering cells to the wound using a product or a composition as described herein.

MAPC

Human MAPCs are described in U.S. Pat. No. 7,015,037. MAPCs have been identified in other mammals. Murine MAPCs, for example, are also described in U.S. Pat. No. 7,015,037. Rat MAPCs are also described in U.S. Pat. No. 7,838,289. These references are incorporated by reference for describing MAPCs, their phenotype and culture.

Isolation and Growth of MAPCs

Methods of MAPC isolation are known in the art. See, for example, U.S. Pat. No. 7,015,037, and these methods, along with the characterization (phenotype) of MAPCs, are incorporated herein by reference. MAPCs can be isolated from multiple sources, including, but not limited to, bone marrow, placenta, umbilical cord and cord blood, muscle, brain, liver, spinal cord, blood or skin. It is, therefore, possible to obtain bone marrow aspirates, brain or liver biopsies, and other organs, and isolate the cells using positive or negative selection techniques available to those of skill in the art, relying upon the genes that are expressed (or not expressed) in these cells (e.g., by functional or morphological assays such as those disclosed in the above-referenced applications, which have been incorporated herein by reference).

Rodent MAPCs have also been obtained by improved methods described in Breyer et al., *Experimental Hematology*, 34:1596-1601 (2006) and Subramanian et al., Cellular Programming and Reprogramming: Methods and Protocols; S. Ding (ed.), *Methods in Molecular Biology*, 636:55-78 (2010), incorporated by reference for these methods. Human MAPCs have been obtained by improved methods that are described in Roobrouck et al. *Stem Cells* 29:871-882 (2011), incorporated by reference for these methods.

MAPCs from Human Bone Marrow as Described in U.S. Pat. No. 7,015,037

MAPCs do not express the common leukocyte antigen CD45 or erythroblast specific glycophorin-A (Gly-A). The mixed population of cells was subjected to a Ficoll Hypaque separation. The cells were then subjected to negative selection using anti-CD45 and anti-Gly-A antibodies, depleting the population of $CD45^+$ and $Gly-A^+$ cells, and the remaining approximately 0.1% of marrow mononuclear cells were then recovered. Cells could also be plated in fibronectin-coated wells and cultured as described below for 2-4 weeks to deplete the cells of $CD45^+$ and $Gly-A^+$ cells. In cultures of adherent bone marrow cells, many adherent stromal cells undergo replicative senescence around cell doubling 30 and a more homogenous population of cells continues to expand and maintains long telomeres.

Alternatively, positive selection could be used to isolate cells via a combination of cell-specific markers. Both positive and negative selection techniques are available to those of skill in the art, and numerous monoclonal and polyclonal antibodies suitable for negative selection purposes are also available in the art (see, for example, Leukocyte Typing V, Schlossman, et al., Eds. (1995) Oxford University Press) and are commercially available from a number of sources.

Techniques for mammalian cell separation from a mixture of cell populations have also been described by Schwartz, et al., in U.S. Pat. No. 5,759,793 (magnetic separation), Basch et al., 1983 (immunoaffinity chromatography), and Wysocki and Sato, 1978 (fluorescence-activated cell sorting).

Cells may be cultured in low-serum or serum-free culture medium. Serum-free medium used to culture MAPCs is described in U.S. Pat. No. 7,015,037. Commonly-used growth factors include but are not limited to platelet-derived growth factor and epidermal growth factor. See, for example, U.S. Pat. Nos. 7,169,610; 7,109,032; 7,037,721; 6,617,161; 6,617,159; 6,372,210; 6,224,860; 6,037,174; 5,908,782; 5,766,951; 5,397,706; and 4,657,866; all incorporated by reference for teaching growing cells in serum-free medium.

Additional Culture Methods

In additional experiments the density at which MAPCs are seeded can vary from about 100 cells/$cm^2$ or about 150 cells/$cm^2$ to about 10,000 cells/$cm^2$, including about 200 cells/$cm^2$ to about 1500 cells/$cm^2$ to about 2000 cells/$cm^2$. The density can vary between species. Additionally, optimal density can vary depending on culture conditions and source of cells. It is within the skill of the ordinary artisan to determine the optimal seeding density for a given set of culture conditions.

Also, effective atmospheric oxygen concentrations of less than about 10%, including about 1-5% and, especially, 3-5%, can be used at any time during the isolation, growth and differentiation of MAPCs in culture.

Cells may be cultured under various serum concentrations, e.g., about 2-20%. Fetal bovine serum may be used. Higher serum may be used in combination with lower oxygen tensions, for example, about 15-20%. Cells need not be selected prior to adherence to culture dishes. For example, after a Ficoll gradient, cells can be directly plated, e.g., 250,000-500,000/$cm^2$. Adherent colonies can be picked, possibly pooled, and expanded.

In one embodiment, high serum (around 15-20%) and low oxygen (around 3-5%) conditions are used for the cell culture. For example, adherent cells from colonies can be plated and passaged at densities of about 1700-2300 cells/$cm^2$ in 18% serum and 3% oxygen (with PDGF and EGF).

In an embodiment specific for MAPCs, supplements are cellular factors or components that allow MAPCs to retain the ability to differentiate into cell types of more than one embryonic lineage, such as, all three lineages. This may be indicated by the expression of specific markers of the undifferentiated state, such as Oct 3/4 (a.k.a. Oct4 or Oct 3A) and/or markers of high expansion capacity, such as, telomerase.

For all the components listed below, see U.S. Pat. No. 7,015,037, which is incorporated by reference for teaching these components.

Stem cells often require additional factors that encourage their attachment to a solid support, such as fibronectin. One embodiment of the present invention utilizes fibronectin. See, for example, Ohashi et al., *Nature Medicine*, 13:880-885 (2007); Matsumoto et al., *J Bioscience and Bioengineering*, 105:350-354 (2008); Kirouac et al., *Cell Stem Cell*, 3:369-381 (2008); Chua et al., *Biomaterials*, 26:2537-2547 (2005); Drobinskaya et al., *Stem Cells*, 26:2245-2256 (2008); Dvir-Ginzberg et al., *FASEB J*, 22:1440-1449 (2008); Turner et al., *J Biomed Mater Res Part B: Appl Biomater*, 82B:156-168 (2007); and Miyazawa et al., *Journal of Gastroenterology and Hepatology*, 22:1959-1964 (2007)).

Once established in culture, cells can be used fresh or frozen and stored as frozen stocks, using, for example, DMEM with 20%-40% FCS and 10% DMSO. In one embodiment, 20% FCS is used. Other methods for preparing frozen stocks for cultured cells are also available to those of skill in the art.

For the purposes of this application, the additional culture methods as well as the other culture methods also apply to bioreactor methods, with respect to the medium components and conditions described above. As an example, in an exemplified embodiment, the oxygen concentration is 5%, serum is about 19% and both EGF and PDGF are added to the medium.

Pharmaceutical Formulations

U.S. Pat. No. 7,015,037 is incorporated by reference for teaching pharmaceutical formulations. In certain embodiments, the cell populations are present within a composition adapted for and suitable for delivery, i.e., physiologically compatible.

In some embodiments the purity of the cells (or conditioned medium) for administration to a subject is about 100% (substantially homogeneous). In other embodiments it is 95% to 100%. In some embodiments it is 85% to 95%. Particularly, in the case of admixtures with other cells, the percentage can be about 10%-15%, 15%-20%, 20%-25%, 25%-30%, 30%-35%, 35%-40%, 40%-45%, 45%-50%, 60%-70%, 70%-80%, 80%-90%, or 90%-95%. Or isolation/purity can be expressed in terms of cell doublings where the cells have undergone, for example, 10-20, 20-30, 30-40, 40-50 or more cell doublings.

The choice of formulation for administering the cells for a given application will depend on a variety of factors. Prominent among these will be the species of subject, the nature of the condition being treated, its state and distribution in the subject, the nature of other therapies and agents that are being administered, the optimum route for administration, survivability via the route, the dosing regimen, and other factors that will be apparent to those skilled in the art. For instance, the choice of suitable carriers and other additives will depend on the exact route of administration and the nature of the particular dosage form.

Final formulations of the aqueous suspension of cells/medium will typically involve adjusting the ionic strength of the suspension to isotonicity (i.e., about 0.1 to 0.2) and to physiological pH (i.e., about pH 6.8 to 7.5). The final formulation will also typically contain a fluid lubricant.

In some embodiments, cells/medium are formulated in a unit dosage injectable form, such as a solution, suspension, or emulsion. Pharmaceutical formulations suitable for injection of cells/medium typically are sterile aqueous solutions and dispersions. Carriers for injectable formulations can be a solvent or dispersing medium containing, for example, water, saline, phosphate buffered saline, polyol (for example, glycerol, propylene glycol, liquid polyethylene glycol, and the like), and suitable mixtures thereof.

The skilled artisan can readily determine the amount of cells and optional additives, vehicles, and/or carrier in compositions to be administered in methods of the invention. Typically, any additives (in addition to the cells) are present in an amount of 0.001 to 50 wt % in solution, such as in phosphate buffered saline. The active ingredient is present in the order of micrograms to milligrams, such as about 0.0001 to about 5 wt %, preferably about 0.0001 to about 1 wt %, most preferably about 0.0001 to about 0.05 wt % or about 0.001 to about 20 wt %, preferably about 0.01 to about 10 wt %, and most preferably about 0.05 to about 5 wt %.

EXAMPLE

MAPC Support Lymphatic Vessel Growth in Lymphedema

MAPCs have Lymphvasculogenic and Lymphangiogenic Potential

Figures 1C, 1D:
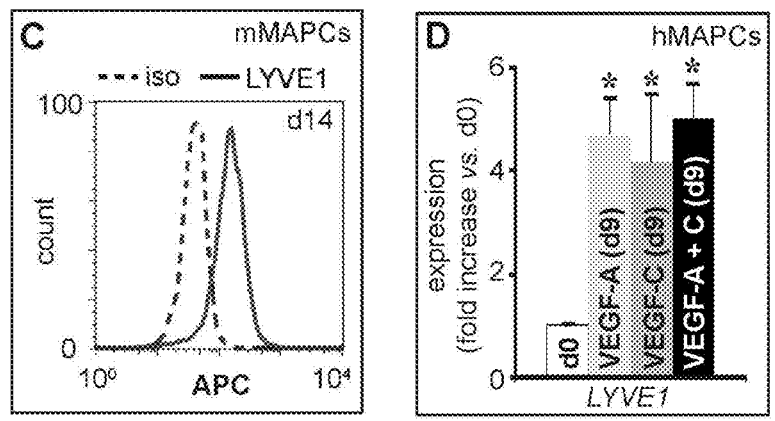
Figure 1E:
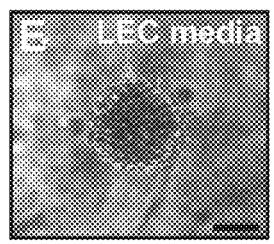
Figure 1F:
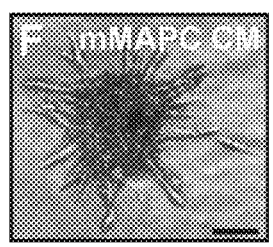
Figure 1G:
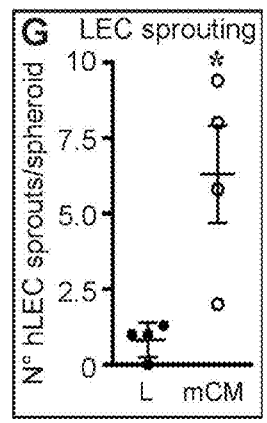
Figure 1H:
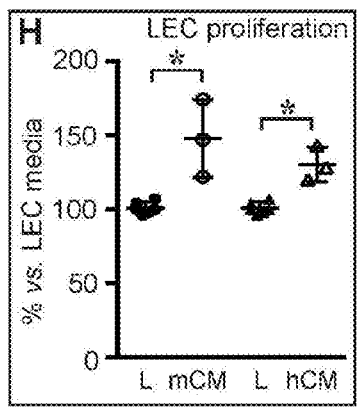
Figure 1I:
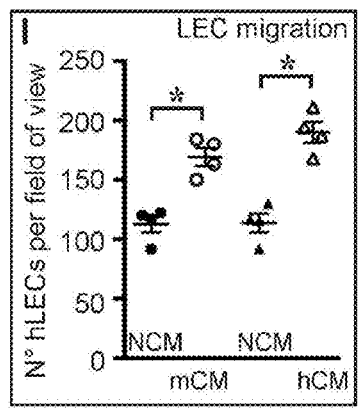
Figure 1J:
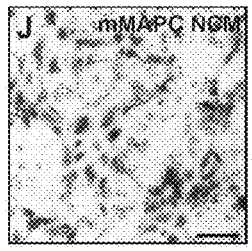
Figure 1K:
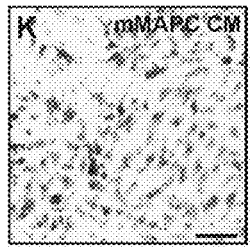
Figure 1L:
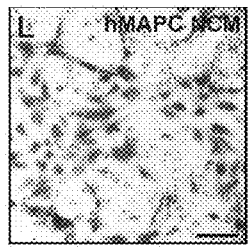
Figure 1M:
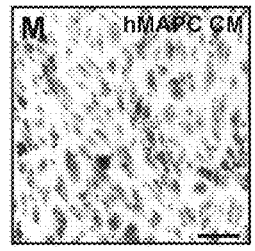

The inventors investigated whether MAPCs have the inherent capacity to give rise to LECs. First, they confirmed that MAPCs gain expression of general EC markers upon VEGF-A exposure (FIG. 1A, B). Prox1, the masterswitch of lymphatic differentiation, was significantly induced in MAPCs at 2w of endothelial differentiation and its expression levels remained stable until 1w later (FIGS. 1A,B). Prox1 induction may also have triggered expression of additional lymphatic genes (i.e., Pdpn and Itg9a), known to be upregulated by forced Prox1 expression(36). A fraction (21±6%) of MAPCs exposed to VEGF-A also expressed LYVE1 (shown at the protein level for mMAPCs; FIG. 1C). Notably, induction of lymphatic marker gene expression in hMAPCs was not further improved in the presence of lymphangiogenic GF VEGF-C(shown for LYVE1 in FIG. 1D; PROX1 fold-induction versus d0 was also comparable upon exposure to VEGF-A, VEGF-C or a combination: 26±10, 26±14 and 26±11, respectively; n=4). COUP-TFII, a transcription factor co-determining lymphatic competence of ECs(36,37), was expressed at high relatively constant levels throughout the differentiation process (not shown). Thus, MAPCs have the inherent capacity to initiate a LEC differentiation program.

The inventors reasoned that MAPCs might have an effect on lymphangiogenesis by cross-talking to LECs, as MAPCs are known to secrete VEGF-A, which is responsible for the trophic effects of MSCs on LECs. 72 h MAPC supernatant significantly stimulated LEC sprouting, proliferation and migration (FIGS. 1E-M). Thus, MAPCs may support the formation of lymphatic vessels by a combination of direct and indirect effects.

MAPCs Contribute to Physiological Lymphangiogenesis During Wound Healing

Figure 2H:
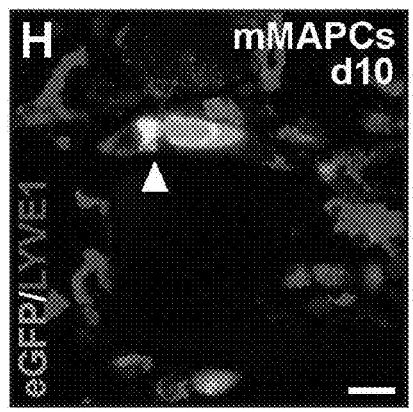
FIG. 2H; Confocal image of a cross-section of a mouse transplanted with eGFP$^+$ mMAPCs 10d earlier revealing occasional co-localization (arrowhead) of eGFP with LYVE1 (red).
Figure 2I:
FIGS. 2I and J; Representative images of cross-sections of wounds treated with PBS (I) or hMAPCs (J) 5d earlier, stained for pancytokeratin (PCK; brown; arrowheads indicate wound borders, horizontal lines indicate distance covered by the epidermis).
Figure 2J:
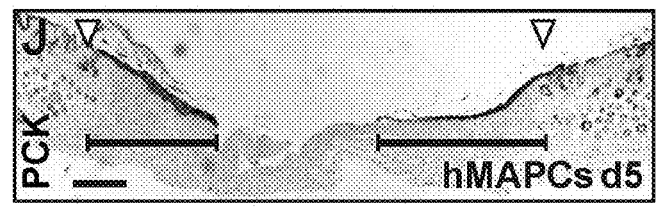
FIG. 2A-2P.
FIG. 2B; Merged brightfield/fluorescent image of the wound (indicated by arrows) area of a mouse transplanted with eGFP$^+$ mMAPCs 4d earlier. Note the mMAPCs are close to blood vessels (indicated by arrowheads) leading towards the wound bed.
FIGS. 2C and D; Representative pictures of CD31-stained (brown) cross-sections of 10d-old wounds from mice treated with PBS (C) or mMAPCs (D).
FIGS. 2E-G; Representative pictures of LYVE1-stained (red) cross-sections of 10d-old wounds from mice treated with PBS (E) or mMAPCs (F), and corresponding quantification (G; data represent mean±SEM. *P<0.05 versus PBS by Mann-Whitney-U test; n=4-5).
FIGS. 2K and L; Representative images of CD31-stained (brown) cross-sections of wounds treated with PBS (K) or hMAPCs (L) 10d earlier.
FIGS. 2M-O; Representative pictures of LYVE1-stained (red) cross-sections of 10d-old wounds from mice treated with PBS (M) or hMAPCs (N), and corresponding quantification (O; data represent mean±SEM. *P<0.05 versus PBS by unpaired Student's t-test; n=6-8).
Figure 2K:
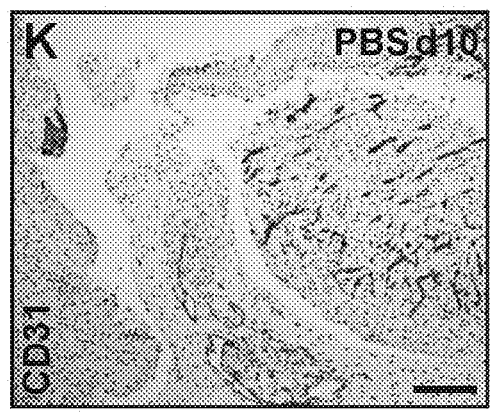
Figure 2L:
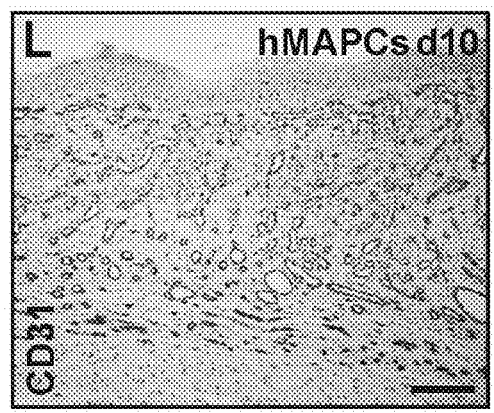
Figure 2M:
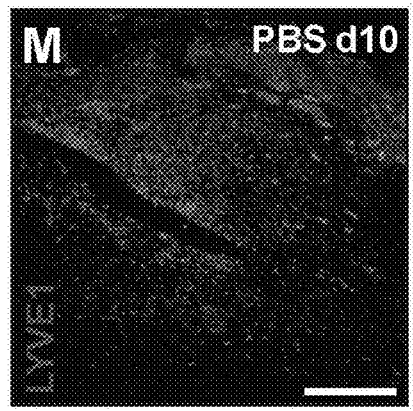
Figure 2N:
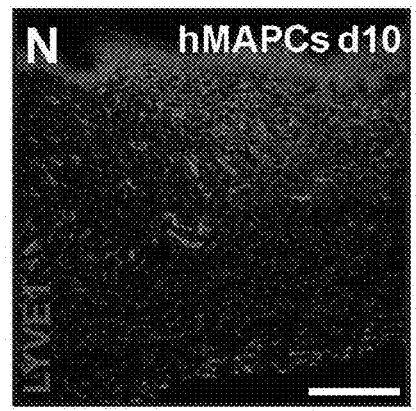
Figure 2O:
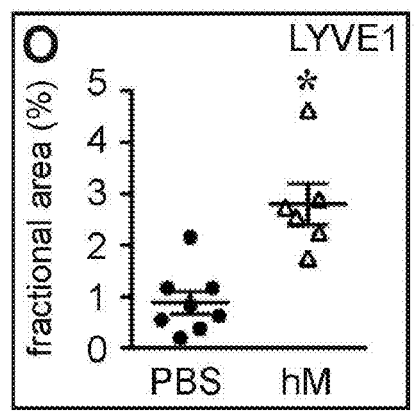
Figure 2P:
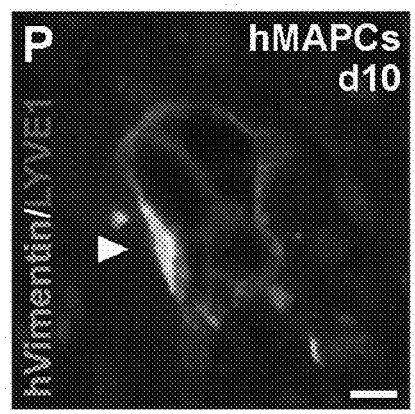
Figure 7A:
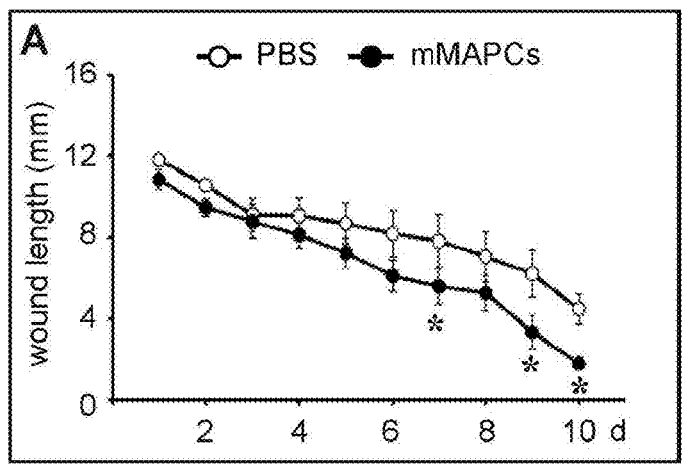
FIGS. 7A-7H.
Figure 7F:
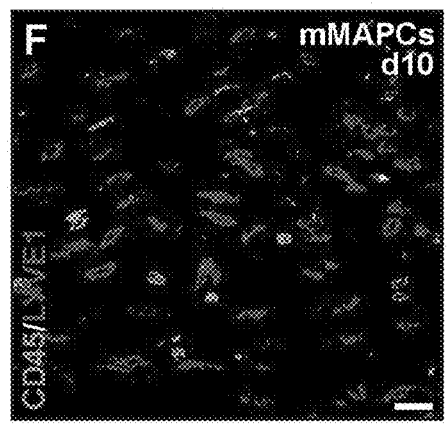
Figure 7B:
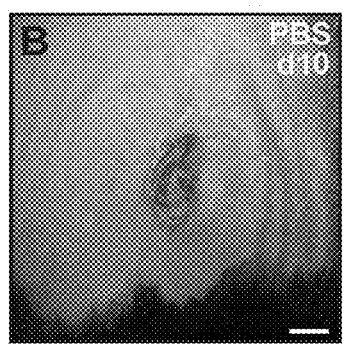
Figure 7C:
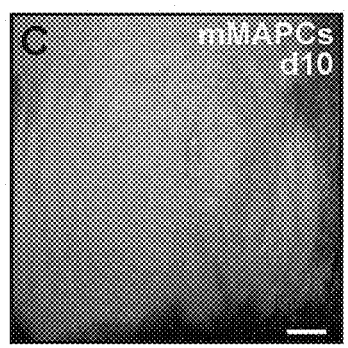
Figure 7G:
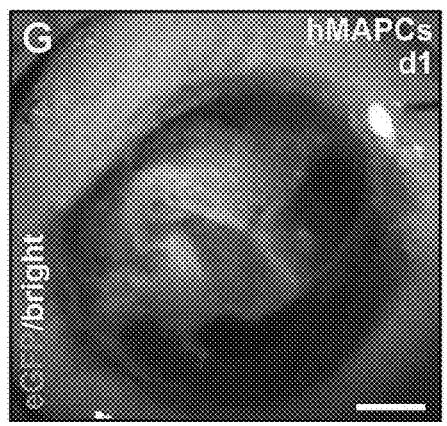
Figure 7D:
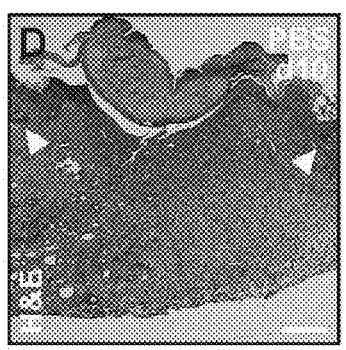
Figure 7E:
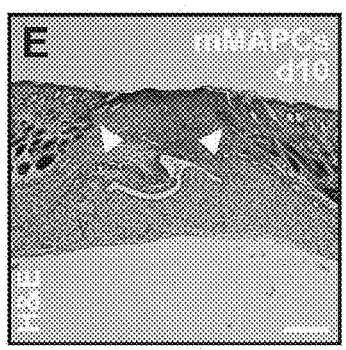
Figure 7H:
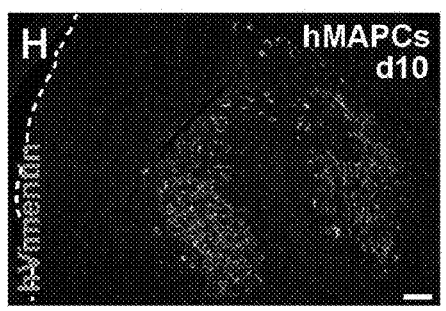

Wound healing requires growth of new blood and lymphatic vessels (Maruyama, K., et al. 2007. *Am J Pathol* (2007) 170:1178-1191). Transplantation of mMAPCs from mice ubiquitously expressing enhanced (e)GFP shortly after a linear back skin incision in C57Bl/6 mice resulted in a significant acceleration of wound closure (FIG. 2A and FIG. 7A) and the occurrence of smaller scars (FIG. 7B-E) compared to PBS-injection. While all mMAPC-injected wounds were completely reepithelialized, 60% of PBS-treated wounds were only partially covered with neo-epidermis at 10d. In vivo fluorescence imaging revealed that 4d after injection, eGFP$^+$ mMAPCs were located in close vicinity to blood vessels growing towards the wound bed (FIG. 2B). In accordance, mMAPC transplantation boosted de novo growth of CD31$^+$ vessels in the wound center by two-fold (number of CD31$^+$ vessels/area (mm$^2$): 76±4 in mMAPC-treated versus 36±16 in PBS-injected mice; n=5, P<0.05 by Mann-Whitney-U test; FIG. 2C,D). In agreement with earlier limb ischemia studies (Aranguren, X. L., et al. *J Clin Invest* (2008) 118:505-514), direct contribution to CD31$^+$ ECs was modest in this wound healing model mMAPCs also significantly increased LYVE1$^+$ lymphatic capillary growth by 3-fold and occasionally contributed to differentiated LECs (FIGS. 2E-H). The vast majority of LYVE1$^+$ cells were lymphatic endothelial cells (LECs) and not macrophage intermediates—previously suggested to contribute to lymphatic vessels in transplanted kidneys (Kerjaschki, D., et al. *Nat Med* (2006) 12:230-234)—since they did not co-localize with CD45, a panleukocytic marker (FIG. 7F).

hMAPCs applied onto circular wounds in athymic nude mice significantly promoted healing. Live imaging and cross-sections through the wound area upon transplantation of hMAPCs showed their homogenous distribution in the wound bed (FIGS. 7G,H). hMAPCs accelerated epithelial coverage (% coverage at 5d: 46±5 in hMAPC-treated versus 7±2 in vehicle-treated wounds; n=6, P<0.05 by Mann-Whitney-U test; FIGS. 2I,J). All wounds were completely reepithelialized at d10 in hMAPC-treated mice versus only 46% of PBS-treated mice. hMAPC transplantation improved wound vascularization by about two-fold (% CD31$^+$ area in the wound borders at 5d and the entire wound at 10d: 11±1 and 13±1 in hMAPC-treated versus 6±1 and 6±1 in PBS-injected wounds; n=6-8, P<0.05 by Student's t-test; FIGS. 2K,L). hMAPCs significantly boosted lymphangiogenesis as evidenced by the three-fold increased LYVE1$^+$ fractional area (FIGS. 2M-O). Double immunofluorescence (IF) staining for Prox1 and smooth muscle α-actin (αSMA) revealed that in this short-duration wound model, the vast majority (97±2%) of lymphatic vessels in the granulation tissue at 10d were capillaries devoid of αSMA coverage. Again, in situ LEC differentiation of hMAPCs happened only occasionally, shown by the co-localization of the hMAPC-derived vimentin signal and LYVE1 staining (FIG. 2P). Thus, MAPCs significantly accelerated wound healing in part by boosting capillary lymphangiogenesis mostly indirectly through a trophic effect on host LECs.

MAPCs Regenerate Lymphatic Vessels in a Secondary Lymphedema Model

Figure 3B:
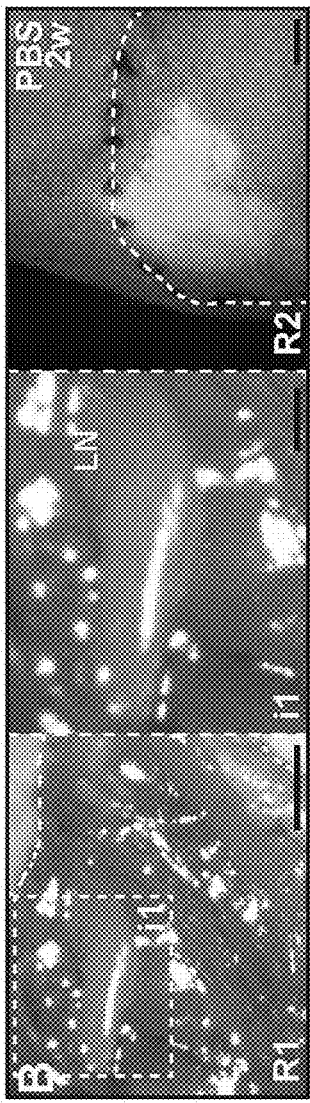
FIG. 3A-3D.
Figure 3C:
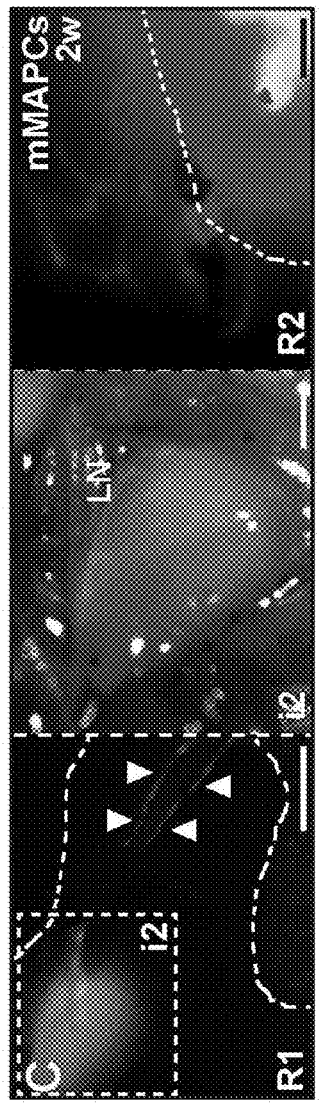
Figure 3D:
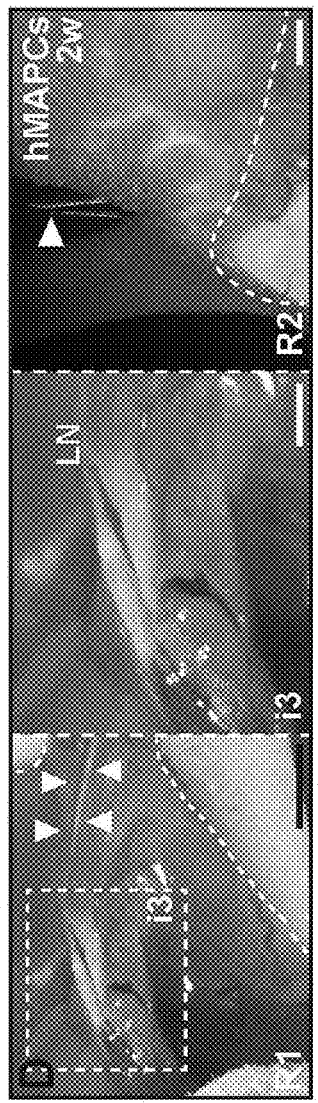

To test the potential of MAPCs to restore lymph flow in secondary lymphedema, lymph drainage to the axillary lymph nodes (LNs) was discontinued by means of a full-thickness skin incision in the abdomen (FIG. 3A) (Saaristo, A., et al. *FASEB J* (2004) 18:1707-1709). This abrogated normal lymph drainage in the majority (7/10) of PBS-treated animals shown by the lack of fluorescent dye crossing the wound border 2w following skin incision (FIG. 3B; Table1). MAPC transplantation around the wound border almost completely (in 5/6 and 6/6 cases for mMAPC- or hMAPC-treated mice, respectively) restored lymph drainage across this border (FIGS. 3C,D; Table 1). While drainage to the axillary LN was only obtained in 1/10 PBS-injected mice, 3/6 mMAPC-injected and 6/6 hMAPC-injected mice showed LN drainage after 2w. In a second set of mice injected with PBS or mMAPCs, fluorescent dye crossed the wound border in 5/5 mMAPC-treated mice and LN drainage was restored in 4/5, while there was no restoration of drainage across the wound border and into the axillary LN in any of the PBS-injected mice 4w after skin incision (Table1). Histological analysis of the skin wound area around the transplantation sites revealed that, in addition to a 1.8-fold expansion of CD31$^+$ blood vessels (FIGS. 8A-D), MAPC-injected mice had a ~two-three-fold increase in Flt4$^+$ (VEGFR3$^+$) and LYVE1$^+$ fractional area in the wound borders (FIGS. 4A-D+8E-H, respectively) 2w after skin incision. The average number of functional lymphatic vessels per cross-section filled with fluorescently-labeled dextran around the incision at 2w was significantly increased by MAPC injection (FIGS. 4E-H). Notably, some mMAPCs persisted until 2-4w, lodged in the vicinity of draining lymphatic vessels and occasionally became part of their endothelial lining (FIGS. 4I-L). Compared to the wound healing models, deep (sparsely) αSMA-coated Prox1$^+$ (pre-) collector vessels were more frequently observed here (FIG. 8I), yet the majority (67±5%) of skin lymphatics was still devoid of αSMA coating. Nevertheless, hMAPC transplantation significantly increased the number of draining (pre-) collectors by 3-fold (Table1). Thus, MAPCs restored the lymphatic functional deficit in secondary lymphedema by bridging the gap in the pre-existing lymphatic network across the wound border.

MAPCs Reconnect Transplanted Lymph Nodes to the Host Lymphatic Network

Figure 9A:
FIGS. 9A-9H.
Figure 9C:
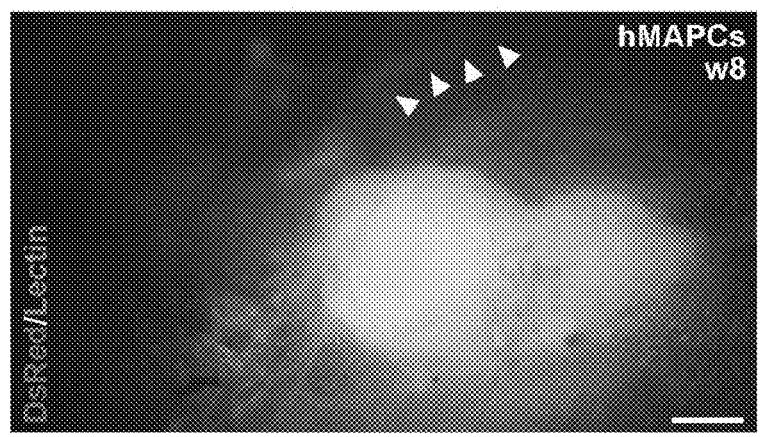
Figure 9B:
Figure 9D:
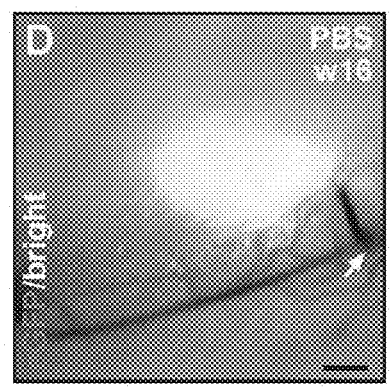
Figure 9E:
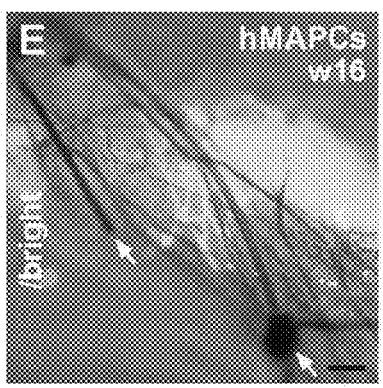
Figure 9F:
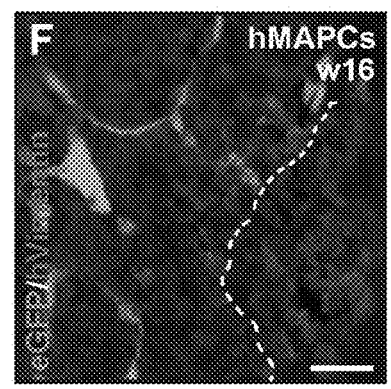
Figure 9G:
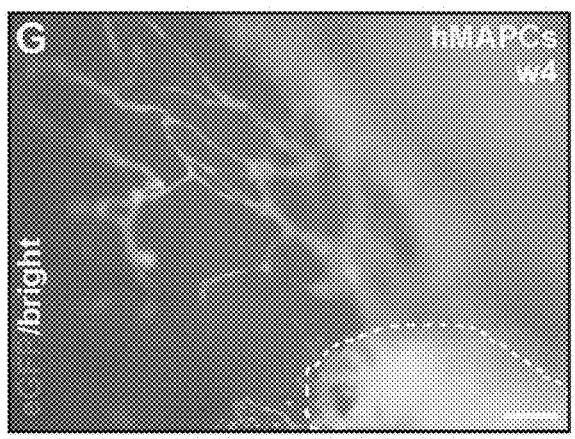
Figure 9H:

Thus far, the results show that MAPC transplantation increases lymphangiogenesis and restores lymphatic drainage mainly by boosting lymphatic capillary growth. However, the underlying problem of secondary lymphedema most often relates to damaged LNs and lymphatic collectors to which the lymphatic capillaries normally connect. Hence, an appropriate remedy must not only imply lymphatic capillary expansion but also restoration of lymphatic collector vessels. A stringent model was applied in which axillary LNs and their surrounding lymphatic (collector) network are surgically ablated, such that drainage of a LN transplanted in this area becomes critically dependent on restoration of lymphatic collectors and their reconnection to the distant lymphatic network (Tammela, T., et al. *Nat Med* (2007) 13:1458-1466). To test the potential of hMAPCs, they were applied in Matrigel® around a transplanted LN derived from mice ubiquitously expressing dsRed or eGFP in the right axillary cavity (FIG. 5A). Transplantation of the LN alone (and covering it with Matrigel® containing PBS) failed to resolve inflammation-induced edema in the right upper limb, evident from the accumulation of interstitial fluid measured by magnetic resonance imaging (MRI) 4w and 16w after surgery upon challenge of the paw with mustard oil—an inflammatory agent (FIGS. 5B,C+9A). At 16w, fluid accumulation was significantly less prominent upon application of hMAPCs around the transplanted LN, suggesting functional restoration of lymph drainage from the front paw to the axillary region (FIGS. 5B,D+9B). Indeed, lymphangiography revealed that lymph fluid drainage was significantly improved in hMAPC-treated mice and that the injected fluorescent dye reached the transplanted LN in ~35% and 50-60% of hMAPC-treated mice, 8w and 16w after transplantation, respectively, a result that was reproduced with two hMAPC clones and not at all with PBS-treated mice (FIGS. 5E-G+9C; Table 2). This suggested that hMAPC transplantation was able to functionally reconnect the transplanted LN to the distant lymphatic network. Notably, while all LNs implanted along with hMAPCs persisted, half of them could not be found back in PBS-injected mice at 16w, suggesting a positive effect of hMAPC transplantation on LN survival (Table 2). Moreover, unlike in hMAPC-treated mice, the mean size of the transplanted LN was decreased in PBS-treated mice (Table 2). Inspection of the skin area leading up to the transplanted LN revealed a two-fold more elaborate blood vascular network in hMAPC-treated mice (FIGS. 6A-C) with significantly more blood vessels in the immediate surroundings of the LNs, compared to PBS-injected mice (FIGS. 6D+9D,E). Some hMAPCs persisted until 16w and were found in the vicinity of the transplanted LN (FIG. 9F). All transplanted LNs in hMAPC-treated mice showed signs of (outward) branching of their internal (lymph)vascular network from 4w onwards, while this was never observed in PBS-treated mice (FIGS. 6E-G+9G,H; Table 2). At 8w, hMAPC transplantation resulted in a significant 4-fold expansion of LYVE1$^+$ lymphatic vessels in the area surrounding the LN as compared to PBS-treatment (FIGS. 6H-J). Finally, to test whether the beneficial effect of hMAPCs was related to functional reconnection of lymphatic collector vessels, αSMA/Prox1 IF stainings were performed on cross-sections taken from the area around the transplanted LNs and found lymph-filled Prox1$^+$αSMA$^+$ collectors (FIGS. 6K-M). Collector identity was confirmed by negative staining for LYVE1 (FIG. 6N). Collectively, hMAPCs restored lymph drainage following LN transplantation by promoting LN survival and outward branching and by reconnecting the transplanted LN to the endogenous vessel network through collector vessels.

Methods

MAPC Derivation and Differentiation

The mMAPC clone was derived from BM of adult C57Bl/6 mice with ubiquitous eGFP expression (C57Bl/6-Tg-eGFP). mMAPCs were derived and maintained under low $O_2$ (5%) and low-serum (2%) conditions, as described (Aranguren, X. L., et al. 2008. *J Clin Invest* (2008) 118: 505-514.). hMAPC clones were established according to derivation and culture methods described earlier (Roobrouck, V. D., et al. *Stem Cells* (2011) 29:871-882.). Cell cultures were routinely tested for *mycoplasma* contamination. Endothelial differentiation was performed by exposure to recombinant (r)hVEGF-A$_{165}$ or rhVEGF-C(R&D Systems), as described (Roobrouck, V. D., et al. *Stem Cells* (2011) 29:871-882). The references that describe the MAPC derivation above are incorporated by reference for these methods.

Human MAPCs were isolated from bone fragments (femur) and hMab isolated from skeletal muscle fragments (quadriceps femoris) of children (5- to 15-year old) undergoing orthopedic surgery, after obtaining informed consent in accordance with the guidelines of the Medical Ethics Committee of the University Hospitals Leuven. hMAPCs were generated by flushing the bone fragment and plating the total cell fraction at 0.5×10$^6$ cells per centimeter square in medium consisting of 60% Dulbecco's modified Eagle's medium (DMEM) low glucose (Gibco, Invitrogen, Carlsbad, Calif., www.invitrogen.com), 40% MCDB-201 (Sigma-Aldrich, St. Louis, Mo., www.sigmaaldrich.com), supplemented with 50 nM dexamethasone, 10$^{-4}$ M L-ascorbic acid, 1× selenium-insulin-transferrin (ITS), 0.5× linoleic acid-bovine serum albumin (all from Sigma-Aldrich), 1% penicillin/streptomycin (Gibco, Invitrogen), along with 2% Serum Supreme (Lonza BioWhittaker, Basel, Switzerland www.Lonza.com), and human platelet derived growth factor BB (PDGF-BB) (R&D Systems, Minneapolis, Minn., www.mdsystems.com) and human EGF (Sigma-Aldrich) (both 10 ng/ml). Human MAPC cultures were maintained under hypoxic conditions (5% $O_2$) in a 5.5% $CO_2$ humidified incubator at a density of 400 cells per centimeter square and were passaged every 2-3 days. Clonal populations were obtained by plating 5 cells per well in a 96-well or 48-well plate between passages 2 and 12.

Isolation and culture of the cells can also be performed as previously described in Reyes, M., et al. *J Clin Invest* (2002) 109:337-346. Bone marrow is obtained from healthy donors. Bone marrow mononuclear cells obtained by Ficoll-Paque density gradient centrifugation are depleted of CD45$^+$ and glycophorinA$^+$ cells by means of micromagnetic beads. The eluted cells are 99.5% negative for both CD45 and glyA. Cells are plated into 96-well plates at a concentration of 5×10$^3$ cells/200 µl. This is done in the same medium described above. When cells are around 50% confluent they are trypsinized and passaged into bigger plates at a concentration of 2×10$^3$-8×10$^3$/cm$^2$ and further expanded. Isolation and culture of the cells can also be performed as previously described in Reyes et al. *Blood* 98:2615-2625. The method is essentially the same as that just described except that, after collecting the cells that are glyA and CD45, cells can be plated into 96-well plates at a concentration of 5-10×10$^3$/ml. In all these conditions the medium is the same. These references are incorporated by reference for reporting methods for the isolation and culture of the cells.

Murine cells were derived from BM of C57BL/6 mice with ubiquitous GFP expression. mMAPCs were derived and maintained under low $O_2$ (5%) and low-serum (2%) conditions (Ulloa-Montoya, F., et al. *Genome Biol.* (2007) 8:R163.). The mMAPCs can also be derived according to Breyer et al. *Experimental Hematology* 34:1596-1601 (2006). These references are incorporated by reference for providing the methods of deriving the cells.

RNA Isolation, cDNA Preparation, qRT-PCR and Flow Cytometry

Total RNA from cell lysates was extracted using Trizol® reagent (Invitrogen) or RLT lysis buffer (Qiagen). mRNA was reverse transcribed using Superscript III Reverse Transcriptase (Invitrogen) and cDNA underwent 40 amplification rounds (primer sequences are listed in Table 3) on an ABI PRISM 7700 cycler, PerkinElmer/Applied Biosystems) for SYBR-Green-based qRT-PCR, as described (Aranguren, X. L., et al. *J Cell Sci* (2013) 126:1165-1175). mRNA levels were normalized using GAPDH as housekeeping gene. To analyze LYVE1 expression on the surface of differentiated mMAPCs, cells were harvested by gentle trypsinization and analyzed by FACS as described in the extended methods.

In Vitro LEC Functional Assays

Cell culture and CM collection. Human lung LECs were purchased from Lonza (Merelbeke, Belgium) and cultured in EBM2 supplemented with EGM-2-MV bulletkit (Lonza). For CM collection, MAPCs were seeded at high density in serum-free basal media and CM was collected after 72 h and frozen in aliquots at −80° C. until further use.

LEC proliferation.

LECs were seeded at 2,000 cells/cm$^2$ in regular LEC growth medium onto gelatin-coated 96-well plates. Following their attachment, medium was replaced by a 1:1 mix of serum-free LEC medium and MAPC-CM or 100% serum-free LEC medium as reference condition. After 24 h, cell proliferation was assessed with the WST-1 cell proliferation assay kit (Cayman Chemical).

LEC Migration.

Transwell inserts (containing polycarbonate filters with 8 µm pore size; Costar, Corning) were coated overnight with gelatin. The bottom compartment of a 24-well plate was filled with non-conditioned media (NCM) or MAPC-CM. Following rehydration, inserts were placed into the 24-well plate and each was loaded with EGM-2-MV/0.5% FBS containing 5×10$^4$ LECs. Following incubation for 24 h at 37° C./5% $CO_2$, cells were fixed in methanol and stained with Wright-Giemsa's staining solution (Sigma WG32). Inserts were lifted and cells on the upper side of the membranes were removed. Pictures of the inserts were taken and transmigrated cells were manually counted.

LEC Sprouting.

LEC spheroids were allowed to form by applying 25 µl droplets (containing 1,000 LECs in a 20% methylcellulose/EGM-2-MV mixture) onto non-attachment plates and incubating them upside down at 37° C./5% $CO_2$. The next day, spheroids were carefully washed in PBS/2% FBS, collected by gentle centrifugation, resuspended in methylcellulose/FBS/collagen (Purecol Advanced Biomatrix) and seeded into 24-well plates. Following incubation for 30 min at 37° C./5% $CO_2$, mMAPC-CM (1:1 mix with serum-free LEC media) or 100% serum-free LEC media as reference condition was added on top of the collagen/spheroid gel. Pictures were taken 24 h later and the number of sprouts per spheroid was determined by manual counting.

Mouse Models

As MAPCs do not express MHC-I and—consequently—are sensitive to NK cell-mediated clearance, all mice were injected i.p. with anti-asialo GM1 Ab's (Wako Chemicals, Osaka, Japan) 1-2 h before transplantation and every 10d thereafter. These antibodies selectively eliminate NK cells without affecting macrophage or lymphocyte function (Seaman, W. E., et al. *J Immunol* (1987) 138:4539-4544).

Linear Wound Model:

At day 0, a 12-mm linear skin incision was inflicted on the back of anesthetized 12-w-old C57Bl/6 male mice Immediately after wounding, mice were injected in the muscle fascia underneath the skin wound with $1\times10^6$ mMAPCs (resuspended in PBS) or PBS alone divided over three equally spaced injection spots. To avoid wound infection, mice were housed individually in cages without bedding. Wound dimensions were measured daily under anesthesia using digital calipers (VWRI819-0012, VWR). At d4, brightfield and fluorescence pictures of the wound area were taken and at d10, mice were euthanized, the residual skin wound and underlying muscle tissue were dissected out, fixed and prepared for embedding.

Circular Wound Model:

At day 0, 12-w-old athymic nude Foxn1 male mice (Harlan) were anesthetized and under sterile and temperature-controlled (37° C.) conditions, standardized full-thickness wounds were made with a 0.5 cm biopsy puncher (Stiefel Laboratories, Offenbach am Main, Germany) on the back of the mouse. A silicone ring was sutured around the wound and wounds were treated with PBS or $5\times10^5$ hMAPCs. In a subset of mice, hMAPCs were transduced with an eGFP-encoding lentivirus before transplantation. An occlusive dressing (Tegaderm™, 3M, Diegem, Belgium) was used to keep the wound moist and was renewed every other day. At 5d or 10d after wounding, mice were euthanized, skin wounds were dissected out, rinsed and post-fixed. Following fixation, skin fragments were separated in two equal pieces at the midline of the wound and processed for embedding.

Figure 3A:
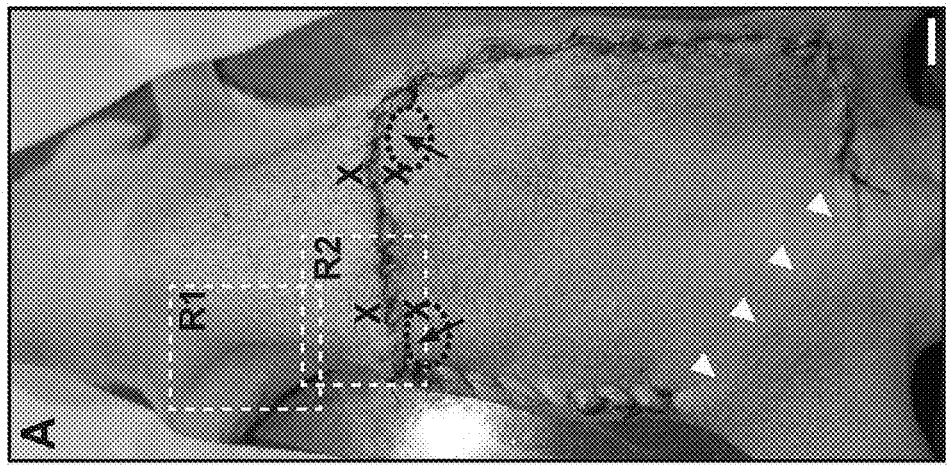

Skin Flap Model:

At day 0, 12-w-old athymic nude Foxn1 male mice (Harlan) were anesthetized and the lymphatic network in the abdominal skin was severed by elevating an epigastric skin flap and suturing it back to its original position, as described (Saaristo, A., et al. *FASEB J* (2004) 18:1707-1709). Continuous blood supply to the flap was insured by retaining a vascular pedicle (FIG. 3A). One day after resuturing the skin flap, $1\times10^6$ mMAPCs, $1\times10^6$ hMAPCs or PBS (divided over 4 injection spots; FIG. 3A) were injected around the wound edges. Two or 4w later, the axillary regions were exposed and axillary LN drainage was monitored by microlymphangiography after intradermal injection of FITC-dextran (MW 2,000 kDa, Sigma-Aldrich; hMAPCs) or Rhodamin-B-isothiocyanate-dextran (MW 70 kDa, Sigma-Aldrich; mMAPCs) under the wound border (FIG. 3A). Brightfield and fluorescence pictures were taken at 15 min and mice were subsequently euthanized, the skin wound area around the cell engraftment/microlymphangiography areas excised, fixed and processed for embedding.

LN Transplantation Model:

At day 0, 12-w-old athymic nude Foxn1 female mice (Harlan) were anesthetized and to visualize the LNs, the right axilla region was exposed and mice were injected with a 3% Evans Blue solution in the palm of the right paw after which LNs were removed (along with the surrounding lymphatic (collector) vessels). A pocket just caudal of the axillary vessels was prepared. Donor LNs were dissected from mice ubiquitously expressing DsRed (B6.Cg-Tg (CAG-DsRed*MST)1Nagy/J; for mice receiving hMAPCs or PBS and followed up for 4w or 8w) or enhanced (e)GFP (C57BL/6-Tg(CAG-EGFP)1Osb/J; for mice receiving hMAPCs or PBS and followed up for 4w or 16w) and cut in two halves through the hilus. The cut LN was subsequently implanted into the recipient pocket and fixed in place with permanent sutures (Monosof™). Cold GF-reduced Matrigel® (Beckton Dickinson) mixed with $0.5\times10^6$ hMAPCs or PBS was applied into the pocket and allowed to solidify. The skin was subsequently closed and the wound covered with Tegaderm™ dressing. Four, eight or sixteen weeks later, mice were anesthetized and subjected to microlymphangiography following injection of FITC-conjugated *L. esculentum* lectin (Vector Laboratories; in DsRed$^+$ LN recipients) or Texas Red-conjugated *L. esculentum* lectin (in eGFP$^+$ LN recipients) in the palm of the right paw. Drainage of the implanted LN was monitored for 15 min and brightfield and fluorescence pictures were taken at the end. Mice were subsequently euthanized, the axilla regions containing the transplanted LN excised, fixed and processed for embedding. Two additional sets of mice were subjected to in vivo MRI, following inflammatory stimulation by injection of mustard oil (to elicit vascular hyperpermeability and aggravate edema), as described in the extended methods.

Histology and Morphometry

Morphometric analyses were performed on 7 μm paraffin sections, 10 μm cryosections or brightfield pictures of exposed skin regions by blinded observers. Lymphatic (determined on LYVE1-, Flt4- or Prox1/αSMA-stained sections) or blood (determined on CD31-stained sections) vessel density and epithelial coverage (determined on pancytokeratin-stained sections) was scored on at least 10 randomly chosen fields per mouse, covering a distance of 700 μm. Functional lymphatics (determined on cryosections of mice injected with fluorescently-labeled dextran) were counted on 8-10 consecutive sections per mouse, thereby scanning the entire wound area visible on each section. The fractional area of the blood vessel network leading up to the transplanted LNs was determined on digitally reconstructed images of the entire region of interest. For stainings on paraffin sections, slides were deparaffinated and rehydrated, cryosections were incubated in PBS for five min prior to the staining procedure. H&E staining was performed as previously described (Aranguren, X. L., et al. *J Clin Invest* (2008) 118:505-514). IF and IHC staining procedures for CD31, Flt4, pancytokeratin, LYVE1 (combined or not with CD45 or vimentin), Prox1/αSMA, vimentin and (Prox1/)eGFP are described in the supplement and a list of primary Ab's is provided in Table 4. All Images were recorded on a Zeiss Axiovert 200M microscope, a Zeiss Axio Imager Z1 or a Zeiss LSM510 confocal microscope equipped with a Zeiss MRc5 camera and Axiovision 4.8 software.

Statistics n in results text and Figure/Table legends designates the number of replicates (i.e., each performed on different passages of a given MAPC clone; in vitro) or separate animals (in vivo). Data normality was tested by the Shapiro-Wilk test. Comparisons among two groups was performed by Student's t-test in case of normal distribution or by Mann-Whitney-U test in cases where data were not normally distributed or normality could not be assumed. Multiple-group comparisons were done by 1-way ANOVA with Tuckey's post-hoc test (normal distribution) or Kruskal-Wallis test with Dunn's post-hoc test (no normality assumption). Wound size was evaluated by repeated measure ANOVA, followed by Fisher least-significant-difference test. All analyses were performed with Graphpad Prism (version 6.0).

Extended Methods

MAPC Derivation and Differentiation

The murine (m)MAPC clone was derived from BM of adult C57Bl/6 mice with ubiquitous eGFP expression (C57Bl/6-Tg-eGFP). mMAPCs were derived and maintained under low $O_2$ (5%) and low-serum (2%) conditions, as previously described (Aranguren, X. L., et al. *J Clin Invest* (2008) 118:505-514). Human (h)MAPC clones were established at KU Leuven (clone 1 or hMAPC1 at the Endothelial Cell Biology Unit; clone 2 or hMAPC2 at the Stem Cell Institute Leuven), according to derivation and culture methods described earlier (Roobrouck, V. D., et al. *Stem Cells* (2011) 29:871-882). Cell cultures were routinely tested for *mycoplasma* contamination. Endothelial differentiation was performed by exposure of the cells to recombinant (r)hVEGF-$A_{165}$ or rhVEGF-C(both from R&DSystems), as described (Roobrouck, V. D., et al. *Stem Cells* (2011) 29:871-882).

RNA Isolation, cDNA Preparation, qRT-PCR and Flow Cytometry

Total RNA from cell lysates was extracted using Trizol® reagent (Invitrogen) or RLT lysis buffer (Qiagen). mRNA was reverse transcribed using Superscript III Reverse Transcriptase (Invitrogen) and cDNA underwent 40 amplification rounds on an ABI PRISM 7700 cycler PerkinElmer/Applied Biosystems) for SYBR-Green-based qRT-PCR, as described (Aranguren, X. L. et al. *J Cell Sci* (2013) 126: 1164-1175.). Primer sequences for qRT-PCR are listed in Table 3. mRNA levels were normalized using GAPDH as housekeeping gene. To analyze LYVE1 expression on the surface of differentiated mMAPCs, cells were harvested by gentle trypsinization, washed with FACS staining buffer (PBS+1 mmol/L EDTA+25 mmol/L HEPES+1% BSA) and incubated with primary antibody (Upstate) or the corresponding rabbit IgG isotype for 20 min at room temperature in the dark. After washing with FACS buffer, cells were incubated with biotinylated goat-anti-rabbit secondary antibodies for 20 min at room temperature in the dark. Next, samples were washed and incubated in the dark for 20 min with allophycocyanin (APC)-labeled streptavidin. To select for viable cells, 7-AAD was added 10 min before running the samples on a FACS Aria I (Beckton Dickinson) for analysis.

In Vitro LEC Functional Assays

Cell Culture and Conditioned Media Collection.

Human lung LECs were purchased from Lonza (Merelbeke, Belgium) and cultured in EBM2 supplemented with EGM-2-MV bulletkit (Lonza). For CM collection, MAPCs were seeded at high density in serum-free basal media and CM was collected after 72 h and frozen in aliquots at −80° C. until further use.

LEC Proliferation.

To test the effect of MAPC-CM on LEC proliferation, LECs were seeded at a density of 2,000 cells/cm$^2$ in regular LEC growth medium onto gelatin-coated 96-well plates. Following their attachment, medium was replaced by a 1:1 mix of serum-free LEC medium and MAPC-CM or 100% serum-free LEC medium as reference condition. After 24 h, cell proliferation was assessed with the WST-1 Cell Proliferation Assay kit. Briefly, 10 µl of WST-1 mixture was added to each well, cells were incubated at 37° C. for 2 h and the absorbance of each well was measured on a Bio-Tek microplate reader (BRS, Belgium) at a wavelength of 450 nm.

LEC Migration.

To estimate the effect of MAPC-CM on LEC migration, a Boyden chamber assay was performed. Briefly, transwell inserts (containing polycarbonate filters with 8 µm pore size; Costar, Corning) were coated overnight with 0.2% gelatin. The bottom compartment of a 24-well plate was filled with 0.3 ml NCM or with 0.3 ml of mMAPC or hMAPC-CM. Following rehydration for 1 h with deionized water, inserts were placed into the 24-well plate and each was loaded with 0.3 ml EGM-2-MV/0.5% FBS containing 5×10$^4$ LECs. Following incubation for 24 h at 37° C./5% $CO_2$, cells were fixed in methanol for 30 min at −20° C. Next, cells were stained with Wright-Giemsa's staining solution (Sigma WG32) for 7 min and rinsed with deionized water for 10 min. Inserts were lifted and cells on the upper side of the membranes were removed by gentle rubbing using a cotton swab. Pictures of the inserts were taken with a Zeiss MRc5 camera mounted onto an Axiovert200M microscope and equipped with Axiovision 4.8 software, and transmigrated cells were manually counted in 3 random fields per insert at 20× magnification.

LEC sprouting. To test the effect of mMAPC-CM on LEC sprouting, LEC spheroids were allowed to form by applying 25 µl droplets (containing 1,000 LECs in a 20% methylcellulose/EGM-2-MV mixture) onto non-attachment plates and incubating them upside down at 37° C./5% $CO_2$. The next day, spheroids were carefully washed in PBS/2% FBS, collected by gentle centrifugation, carefully resuspended in methylcellulose/FBS/collagen (Purecol Advanced Biomatrix) and seeded into 24-well plates (0.5 ml/well). Following incubation of 30 min at 37° C./5% $CO_2$, 0.5 ml mMAPC-CM (1:1 mix with serum-free LEC media) or 100% serum-free LEC media as reference condition was added on top of the collagen/spheroid gel. Pictures were taken 24 h later with a Zeiss MRm camera mounted on a Zeiss Axiovert200M microscope and the number of sprouts per spheroid was determined by manual counting.

Mouse Models

As MAPCs do not express MHC-I and—consequently—are sensitive to NK cell-mediated clearance, all mice were injected i.p. with 20 µl anti-asialo GM1 Ab's (Wako Chemicals, Osaka, Japan; 20× diluted in PBS) 1-2 h before transplantation and every 10d thereafter. These antibodies selectively eliminate NK cells without affecting macrophage or lymphocyte function (Seaman, W. E., et al. *J Immunol* (1987) 138:4539-4544.).

Linear wound model: At day 0, a 12-mm linear skin incision was inflicted with a scalpel on the back of 12-w-old C57Bl/6 male mice after they were anesthetized with a mixture of 100 mg/kg ketamine and 10 mg/kg xylazine Immediately after wounding, mice were injected in the muscle fascia underneath the skin wound with 1×10$^6$ mMAPCs (resuspended in PBS) or PBS alone divided over three equally spaced injection spots. To avoid wound infection, mice were housed individually in cages without bedding. Wound dimensions were measured daily under isoflurane anesthesia using digital calipers (VWRI819-0012, VWR). At day 4, brightfield and fluorescence pictures of the wound area were taken with a Zeiss MRc5 camera mounted on a Zeiss Lumar microscope. At d10, mice were euthanized, the residual skin wound and underlying muscle tissue were dissected out, fixed in zinc-paraformaldehyde and prepared for embedding in paraffin or optimal cutting temperature (OCT) and sectioning.

Circular Wound Model:

At day 0, 12-w-old athymic nude Foxn1 male mice (Harlan) were anesthetized with an i.p. injection of ketamine/xylazine. Atropine (0.01 mg/kg) was administered i.p. as premedication. Under sterile and temperature-controlled (37° C.) conditions, standardized full-thickness wounds were made with a 0.5 cm biopsy puncher (Stiefel Laboratories, Offenbach am Main, Germany) on the back of the mouse in the mid-dorsal region. A silicone ring was fixed (using Histoacryl tissue adhesive, Braun, Diegem, Belgium) and sutured around the wound and wounds were treated with saline or $5 \times 10^5$ hMAPCs. In a separate subset of mice, hMAPCs were transduced with an eGFP-encoding lentivirus before transplantation. An occlusive dressing (Tegaderm™, 3M, Diegem, Belgium) was used to keep the wound moist. All wounded mice were housed individually to avoid fighting and to prevent removal of the occlusive wound dressing. Every other day, the occlusive dressing was renewed under isoflurane anesthesia. At 5d or 10d after wounding, mice were euthanized and square skin fragments including the circular wound area and a rim of normal skin were dissected out, rinsed in PBS and post-fixed overnight at 4° C. using zinc-paraformaldehyde. Following fixation, skin fragments were separated in two equal pieces at the midline of the wound and processed for paraffin or OCT embedding and sectioning.

Skin Flap Model:

At day 0, 12-w-old athymic nude Foxn1 male mice (Harlan) were anesthetized with an i.p. injection of ketamine/xylazine. The lymphatic network in the abdominal skin was severed by elevating an epigastric skin flap and suturing it back to its original position, as previously described (Saaristo, A., et al. *FASEB J* (2004) 18:1707-1709.). Continuous blood supply to the flap was insured by retaining a vascular pedicle including the right inferior epigastric artery and vein (FIG. 3A). One day after resuturing the skin flap, $1 \times 10^6$ mMAPCs, $1 \times 10^6$ hMAPCs or PBS (divided over 4 injection spots; FIG. 3A) were injected around the wound edges. Two or four weeks later, the axillary regions were exposed and axillary lymph node drainage was monitored by microlymphangiography for 15 min after intradermal injection of 10 µl FITC-dextran (MW 2,000 kDa, Sigma-Aldrich; hMAPCs) or 10 µl Rhodamin-B-isothiocyanate-dextran (MW 70 kDa, Sigma-Aldrich; mMAPCs) under the wound border (FIG. 3A). Brightfield and fluorescence pictures were taken at 15 min with a Zeiss MRc5 camera mounted onto a Zeiss Lumar microscope. Mice were subsequently euthanized, the skin wound area around the cell engraftment/microlymphangiography areas excised, fixed and processed for paraffin or OCT embedding and sectioning.

Lymph Node Transplantation Model:

At day 0, 12-w-old athymic nude Foxn1 female recipient mice (Harlan) were anesthetized with an i.p. injection of ketamine (100 mg/kg) and xylazine (10 mg/kg). To visualize the lymph nodes, the right axilla region was exposed and mice were injected with a 3% Evans Blue solution in the palm of the right paw after which lymph nodes were removed along with the surrounding lymphatic (collector) vessels. A pocket just caudal of the axillary vessels, aligned by the lateral axillary fat pad, the *M. pectoralis* and the *M. latissimus dorsi* was prepared. Donor lymph nodes were dissected from mice ubiquitously expressing DsRed (B6.Cg-Tg(CAG-DsRed*MST)1Nagy/J; for mice receiving hMAPCs or PBS and followed up for 4w or 8w) or enhanced (e)GFP (C57BL/6-Tg(CAG-EGFP)1 Osb/J; for mice receiving hMAPCs or PBS and followed up for 4w or 16w) and cut in two halves through the hilus. The cut lymph node was subsequently implanted into the recipient pocket (hilus oriented medially and cut surface facing upwards) and fixed in place with two permanent sutures (using 9-0 nylon non-absorbable suture, Monosof™). Cold growth factor-reduced Matrigel® (100 µl; Beckton Dickinson) mixed with $0.5 \times 10^6$ hMAPCs or PBS was applied into the pocket and allowed to solidify for 10 min. The skin was subsequently closed and the wound covered with Tegaderm™ dressing. Four, eight or sixteen weeks later, mice were anesthetized with a ketamine/xylazine mixture and subjected to microlymphangiography following injection of 10 µl FITC-conjugated *L. esculentum* lectin (Vector Laboratories; in recipients of DsRed$^+$ donor lymph nodes) or 10 µl Texas Red-conjugated *L. esculentum* lectin (in recipients of eGFP$^+$ lymph nodes) in the palm of the right paw. Drainage of the implanted lymph node was monitored for 15 min and brightfield and fluorescence pictures were taken at the end with a Zeiss MRc5 camera mounted onto a Zeiss Lumar microscope. Mice were subsequently euthanized, the axilla regions containing the transplanted lymph node excised, fixed and processed for paraffin or OCT embedding and sectioning. Two additional sets of mice were subjected to in vivo magnetic resonance imaging (MRI; as described (Tammela, T., et al. *Nat Med* (2007) 13:1458-1466) at 4w or 16w after lymph node transplantation. Briefly, mice were anesthetized with isoflurane and mustard oil (diluted ⅕ in mineral oil) was applied with a cotton stick on both fore limbs for 2×15 min to elicit vascular hyperpermeability and aggravate edema. Mice were allowed to recover for another 30 min before MRI recording. Temperature and respiration were monitored throughout the experiment and maintained at 37° C. and 100-120 breaths per min. MR images were acquired with a 9.4T Biospec small animal MR scanner (Bruker Biospin, Ettlingen, Germany) equipped with a horizontal bore magnet and an actively shielded gradient set of 600 mT per m (117 mm inner diameter) using a 7 cm linearly polarized resonator for transmission and an actively decoupled dedicated 2 cm diameter surface coil for receiving (Rapid Biomedical, Rimpar, Germany) After the acquisition of 2D localization scans; 3D $T_2$ weighted images, 2D $T_2$ parameter maps and 2D diffusion weighted images were acquired to determine the level of edema. Specific parameters were: 3D rapid acquisition with refocused echoes (RARE) sequence, repetition time (TR): 1300 ms, effective echo time (TE): 22.9 ms, rare factor: 6, matrix size: 256× 48×48, field of view (FOV): 2.5×0.7×1.5 cm, resolution: 98×146×312 µm$^3$; 2D $T_2$ maps: TR: 3500 ms, 10 TE's between: 10-100 ms, matrix size: 256×256, FOV: 2×2 cm, 15 transverse slices with slice thickness: 0.3 mm and gap 0.3 mm, in plane resolution: 78 µm$^2$; diffusion weighted MRI: spin echo sequence; b-value of 1500 s mm$^2$, TR: 25 ms, TE: 3,000 ms, matrix size: 128×128, FOV: 2×2 cm, 8 transverse slices of 1 mm thickness. Processing of the 3D $T_2$ weighted images was done by determining the volume with a signal intensity above a common threshold value using home-written software developed with Mevislab (Mevis Medical Solutions, Bremen, Germany) reported as ratio's between the lymph node implanted site versus the control site. Calculation of the $T_2$ parameter maps of the manually delineated edema of the paws (or an area of the same size and located in the same region in the absence of edema) was done using Paravison 5.1 (Bruker Biospin).

Histology and Morphometry

Morphometric analyses were performed on 7 µm paraffin sections, 10 µm cryosections or brightfield pictures of exposed skin regions by blinded observers. Lymphatic (determined on LYVE1-, Flt4- or Prox1/αSMA-stained sections) or blood (determined on CD31-stained sections) vessel density and epithelial coverage (determined on pancytokeratin-stained sections) was scored on at least 10 randomly chosen fields per mouse, covering a distance of 700 μm. Functional lymphatics (determined on cryosections of mice injected with fluorescently-labeled dextran) were counted on 8-10 consecutive sections per mouse, thereby scanning the entire wound area visible on each section. The fractional area of the blood vessel network leading up to the transplanted lymph nodes was determined on digitally reconstructed images of the entire region of interest. For stainings on paraffin sections, slides were deparaffinated and rehydrated, cryosections were incubated in PBS for five min prior to the staining procedure. H&E staining was performed as previously described (1). For CD31, Flt4 or pancytokeratin immunohistochemical staining, antigen retrieval was performed by boiling in target retrieval solution s1699 (Sigma). After cooling down in TBS, endogenous peroxidase activity was quenched in 0.3% $H_2O_2$ in methanol. Slides were incubated with primary Ab overnight. A list of primary Ab's is provided in Table 4. After washing in TBS, slides were incubated for 2 h with biotinylated rabbit-anti-rat (CD31 and Flt4) or goat anti-mouse (pancytokeratin) Ab's and the detection signal was amplified with a tyramide signal amplification system (Perkin Elmer, NEL700A). Nuclei were revealed by hematoxylin counterstaining and slides were mounted with DPX mountant (Sigma). For LYVE1 immunofluorescence (IF) staining, antigen retrieval was performed by boiling in target retrieval solution s1699 (Sigma). After cooling down in TBS, endogenous peroxidase activity was quenched in 0.3% $H_2O_2$ in methanol. Slides were incubated with primary Ab overnight. After washing in TBS, slides were incubated for 2 h with biotinylated goat-anti-rabbit Ab and the detection signal was amplified with a tyramide-Cy3 or tyramide-fluorescein signal amplification system (Perkin Elmer, NEL704A or NEL701A). When combined with CD45 IF staining, slides were subsequently incubated with primary anti-CD45 Ab overnight, followed by a 2 h incubation with goat-anti-rat-Alexa488. For GFP or vimentin IF staining, antigen retrieval was performed by boiling in citrate buffer (pH=6). After overnight incubation with primary Ab, slides were incubated for 1 h with Alexa-conjugated donkey-anti-chicken (GFP) or goat-anti-mouse (vimentin) Ab's. For combined LYVE1/vimentin IF staining, antigen retrieval was performed by boiling in citrate buffer (pH=6) and tissues were permeabilized by incubation in Triton 0.1% in PBS. After overnight incubation with primary Abs, slides were incubated for 1 h with goat-anti-mouse-Alexa488 and goat-anti-rabbit-Alexa568. For combined Prox1/αSMA IF staining, antigen retrieval was performed by boiling in citrate buffer (pH=6) and tissues were permeabilized by incubation in Triton 0.1% in PBS. After overnight incubation with Prox1 primary Ab, slides were incubated for 1 h with biotin-conjugated goat-anti-rabbit Ab and the detection signal was amplified with a tyramide-Cy3 or tyramide-fluorescein signal amplification system (Perkin Elmer, NEL704A or NEL701A). Slides were subsequently stained with Cy3-conjugated αSMA for 2 h or with unconjugated SMA followed by goat-anti-mouse-Alexa660. For combined Prox1/eGFP IF staining, antigen retrieval was performed by boiling in citrate buffer (pH=6) and tissues were permeabilized by incubation in Triton 0.1% in PBS. After overnight incubation with Prox1 and eGFP primary Ab's, slides were incubated for 1 h with biotin-conjugated goat-anti-rabbit and Alexa488-conjugated donkey-anti-chicken Ab's and the Prox1 detection signal was amplified with a tyramide-Cy3 signal amplification system (Perkin Elmer). IF-stained slides were sealed with ProLong Gold Antifade Reagent with DAPI (Life Technologies; P36931) or without in case nuclei were revealed by Hoechst staining. All Images were recorded on a Zeiss Axiovert 200M microscope, a Zeiss Axio Imager Z1 or a Zeiss LSM510 confocal microscope equipped with a Zeiss MRc5 camera and Axiovision 4.8 software.

Statistics n in results text and Figure/Table legends designates the number of replicates (i.e., each performed on different passages of a given MAPC clone; in vitro) or separate animals (in vivo). Normality of the data was tested by the Shapiro-Wilk test. Comparisons among two groups was performed by Student's t-test in case of normal distribution or by Mann-Whitney-U test in cases where data were not normally distributed or normality could not be assumed. Multiple-group comparisons were done by 1-way ANOVA with Tuckey's post-hoc test (normal distribution) or Kruskal-Wallis test followed by Dunn's post-hoc test (no normality assumption). Wound size was evaluated by repeated measures ANOVA, followed by Fisher least-significant-difference test. All analyses were performed with Graphpad Prism (version 6.0).

Tables

TABLE 1

Lymphangiography in skin flap model

|  | PBS |  | mMAPCs |  | hMAPCs |
|---|---|---|---|---|---|
|  |  |  |  |  |  |
| Day post operation | 14 | 28 | 14 | 28 | 14 |
| Wound border crossing (%) | 30.0 | 0.0 | 83.3 | 100.0 | 100.0 |
| Lymph node filling (%) | 10.0 | 0.0 | 50.0 | 80.0 | 100.0 |
| Dextran⁺Prox1⁺αSMA⁺ (pre-) collectors (average number per cross-section) | 3 ± 1 | ND | ND | ND | 10 ± 3[A] |

Data represent fraction of mice revealing the functional feature mentioned in the left column or the mean±SEM. (PBS: n=10 for each time point; mMAPCs: n=6 for 14d and n=5 for 28d; hMAPCs: n=6). ND, not determined. [A]P<0.05 versus PBS by unpaired Student's t-test.

TABLE 2

Lymphangiography in LN transplantation model

|  | PBS | | | hMAPC1 | | | hMAPC2 | | |
|---|---|---|---|---|---|---|---|---|---|
| Week | 4 | 8 | 16 | 4 | 8 | 16 | 4 | 8 | 16 |
| Survival (%) | 100.0 | 83.0 | 50.0 | 100.0 | 100.0 | 100.0 | 100.0 | 100.0 | 100.0 |
| Size (mm²) | 0.74 ± 0.20 | 0.25 ± 0.10 | 0.35 ± 0.24 | 0.64 ± 0.13 | 1.20 ± 0.18[A] | 1.08 ± 0.12[A] | ND | ND | ND |

TABLE 2-continued

Lymphangiography in LN transplantation model

| | PBS | | | hMAPC1 | | | hMAPC2 | | |
|---|---|---|---|---|---|---|---|---|---|
| Week | 4 | 8 | 16 | 4 | 8 | 16 | 4 | 8 | 16 |
| Branching (%) | 0.0 | 0.0 | 0.0 | 100.0 | 100.0 | 100.0 | 100.0 | 100.0 | 100.0 |
| Filling (%) | 0.0 | 0.0 | 0.0 | 0.0 | 33.3 | 62.5 | 0.0 | 37.5 | 50.0 |

Data represent fraction of mice revealing the functional feature of the transplanted LN mentioned in the left column or mean±SEM. (PBS: n=10, 6 and 6 for 4w, 8w and 16w, respectively; hMAPC1: n=10, 6 and 8 for 4w, 8w and 16w, respectively; hMAPC2: n=6, 8 and 4 for 4w, 8w and 16w, respectively); ND: not determined. $^A$P<0.05 versus corresponding PBS condition by Mann-Whitney-U test.

TABLE 3 qRT-PCR primers

| Gene | 5'-3' forward primer | SEQ ID NO: | 5'-3' reverse primer | SEQ ID NO: |
|---|---|---|---|---|
| Prox1 (M) | CGCGTGGGTTTCTTCTCTGC | 1 | GGGCTGTGCTGTCATGGTCA | 2 |
| Pdpn (M) | GCCAGTGTTGTTCTGGGTTT | 3 | AGAGGTGCCTTGCCAGTAGA | 4 |
| Itga9 (M) | CTGCTTTCCAGTGTTGACGA | 5 | AATGCCCATCTCCTCCTTCT | 6 |
| Flt1 (M) | TGGCCAGAGGCATGGAGT | 7 | TCGCAAATCTTCACCACATGG | 8 |
| Tek1 (M) | GAAACATCCCTCACCTGCAT | 9 | TGGCCTTTTCTCTCTTCCAA | 10 |
| VWF (M) | AAGGAGCAGGACCTGGAAGT | 11 | GCGTGTATGTGAGGATGTGG | 12 |
| Gapdh (M) | CCGCATCTTCTTGTGCAGT | 13 | GAATTTGCCGTGAGTGGAGT | 14 |
| PROX1 (H) | CAGTACTGAAGAGCTGTCTATAACCAGAG | 15 | TCTGAGCAACTTCCAGGAATCTC | 16 |
| PDPN (H) | TGCTCTTCGTTTTGGGAAGC | 17 | TCGCTGGTTCCTGGAGTCAC | 18 |
| ITGA9 (H) | AGGACGCTGATCCCTTGCTA | 19 | GCACTTTGATGGTTCCAGCC | 20 |
| FLT1 (H) | TTTGGATGAGCAGTGTGAGC | 21 | CGGCACGTAGGTGATTTCTT | 22 |
| TEK1 (H) | ACACCTGCCTCATGCTCAGC | 23 | AGCAGTACAGAGATGGTTGCATTC | 24 |
| VWF (H) | TGCTGGTATGGAGTATAGGCAGTG | 25 | CCGGAATGCACGCAGG | 26 |
| GAPDH (H) | TGGTATCGTGGAAGGACTCATGAC | 28 | ATGCCAGTGAGCTTCCCGTTCAGC | 28 |

TABLE 4

List of antibodies for histology

| Antigen | Target species | Supplier, catalog No |
|---|---|---|
| CD31 | mouse | Beckton Dickinson, 557355 |
| LYVE1 | mouse + human | Upstate Biotechnology, 07-538 |
| Pancytokeratin (PCK) | mouse | Sigma, C-2562 |
| Flt4 | mouse | eBioscience, 14-5988-82 |
| Smooth muscle α-actin (SMA) | mouse + human | Sigma C-6148 or A5228 |
| CD45 | mouse | Beckton Dickinson, 553076 |
| Prox1 | mouse + human | Angiobio, 11-002 |
| Vimentin | human | DAKO, Clone V9 |
| eGFP | chicken | Abcam, ab13970 |

What is claimed is:

1. A method to promote wound healing of an ulcer in a subject by administering cells (I) in an effective amount and for a time sufficient to promote the wound healing in the ulcer, wherein the cells (I) are not delivered from a functionalized substrate, wherein the cells (I) are non-embryonic non-germ cells that express CD90 and oct4 or telomerase, are not transformed, are not tumorigenic, and have a normal karyotype.

2. The method of claim 1, wherein the cells (I) express telomerase.

3. The method of either of claims 1 or 2, wherein the cells (I) can differentiate into at least one cell type of at least two of the endodermal, ectodermal, and mesodermal embryonic lineages.

4. The method of claim 3, wherein the cells (I) can differentiate into at least one cell type of each of the endodermal, ectodermal, and mesodermal embryonic lineages.

5. The method of claims 1 or 2, wherein the ulcer is selected from the group consisting of dermal ulcers found in feet, hand, legs, or arms and venous leg ulcers.

6. The method of claim 5, wherein the dermal ulcer is caused by a disease selected from the group consisting of diabetes and sickle-cell anemia.

7. The method of either of claims 1 or 2, wherein the cells (I) are not genetically manipulated.

8. The method of either of claims 1 or 2, wherein the cells (I) are derived from bone marrow.

9. The method of either of claims 1 or 2, wherein the cells (I) are derived from a human.

10. The method of either of claims 1 or 2, wherein the subject is human.

11. The method of claim 1, wherein the wound is caused by insufficient circulation of peripheral blood or lymphatic system.

12. The method of either of claims 1 or 2, wherein the cells (I) are administered to the wound topically.

13. The method of either of claims 1 or 2, wherein the cells (I) are delivered subcutaneously.

14. The method of either of claims 1 or 2, wherein the cells (I) are administered to the wound by injection.

15. The method of either of claims 1 or 2, wherein the cells (I) are administered in liquid cell suspension.

16. The method of either of claims 1 or 2, wherein the cells (I) are administered to the wound using a reservoir.

17. The method of either of claims 1 or 2, wherein the cells (I) are allogeneic.

\* \* \* \* \*